US011873279B2

(12) United States Patent
Gurkan et al.

(10) Patent No.: US 11,873,279 B2
(45) Date of Patent: Jan. 16, 2024

(54) COMPOSITIONS FOR TREATMENT OF OCULAR DISEASES

(71) Applicant: Perfuse Therapeutics, Inc., San Francisco, CA (US)

(72) Inventors: Sevgi Gurkan, Belmont, CA (US); David Floyd, Pennington, NJ (US); Zhongli Ding, Sunnyvale, CA (US)

(73) Assignee: Perfuse Therapeutics, Inc., San Francisco, CA (US)

( * ) Notice: Subject to any disclaimer, the term of this patent is extended or adjusted under 35 U.S.C. 154(b) by 0 days.

(21) Appl. No.: 17/879,627

(22) Filed: Aug. 2, 2022

(65) Prior Publication Data

US 2023/0120974 A1      Apr. 20, 2023

Related U.S. Application Data

(63) Continuation of application No. PCT/US2021/016414, filed on Feb. 3, 2021.

(60) Provisional application No. 63/010,212, filed on Apr. 15, 2020, provisional application No. 62/971,002, filed on Feb. 6, 2020.

(51) Int. Cl.
    *C07D 413/12*      (2006.01)

(52) U.S. Cl.
    CPC ........ *C07D 413/12* (2013.01); *C07B 2200/13* (2013.01)

(58) Field of Classification Search
    CPC .............. C07D 413/12; C07B 2200/13; A61K 31/422; A61K 9/0048; A61P 27/02; A61P 27/06
    See application file for complete search history.

(56) References Cited

U.S. PATENT DOCUMENTS

| 5,364,374 A | 11/1994 | Morrison et al. |
| 6,043,265 A | 3/2000 | Murugesan et al. |
| 7,927,613 B2 | 4/2011 | Almarsson et al. |
| 8,980,874 B2 | 3/2015 | Gulati |
| 2003/0176356 A1 | 9/2003 | Yorio et al. |
| 2004/0063731 A1 | 4/2004 | Eggenweiler et al. |
| 2004/0234611 A1 | 11/2004 | Ahlheim et al. |
| 2007/0116729 A1 | 5/2007 | Palepu |

(Continued)

FOREIGN PATENT DOCUMENTS

| WO | WO-2002/032884 A2 | 4/2002 |
| WO | WO-2010/144477 A2 | 12/2010 |

(Continued)

OTHER PUBLICATIONS

Davenport, et al., "Endothelin." Pharmacological reviews (2016) 68:357-418.

(Continued)

*Primary Examiner* — Kortney L. Klinkel
*Assistant Examiner* — Padmaja S Rao
(74) *Attorney, Agent, or Firm* — Goodwin Procter LLP

(57) ABSTRACT

The present disclosure relates to the discovery that certain ocular diseases may be treated using Edonentan crystalline forms. Specific Edonentan crystalline form can be used alone or in combination with an intra-ocular pressure (TOP) reducing agent, a neuroprotective agent, or an anti-VEGF agent. Using Edonentan crystalline forms, alone or in combination with an additional agent, provides increased perfusion to the retina or reduced IOP in certain ocular diseases and reduces damage to retinal cells.

20 Claims, 9 Drawing Sheets

(56) References Cited

U.S. PATENT DOCUMENTS

| | | |
|---|---|---|
| 2011/0275715 A1 | 11/2011 | Mashima et al. |
| 2016/0331712 A1 | 11/2016 | Georgiou |
| 2016/0346224 A1 | 12/2016 | Macdonald |
| 2018/0362570 A1 | 12/2018 | Ganapati et al. |
| 2019/0015521 A1 | 1/2019 | Roizman |
| 2022/0257505 A1 | 8/2022 | Gurkan et al. |
| 2022/0257568 A1 | 8/2022 | Gurkan et al. |

FOREIGN PATENT DOCUMENTS

| | | |
|---|---|---|
| WO | WO-2016/156639 A1 | 10/2016 |
| WO | WO-2017/217967 A1 | 12/2017 |
| WO | WO-2018/185516 A1 | 10/2018 |
| WO | WO-2019/210194 A1 | 10/2019 |
| WO | WO-2021/158663 A1 | 8/2021 |

OTHER PUBLICATIONS

Francesco Boscia, Current Approaches to the Management of Diabetic Retinopathy and Diabetic Macular Oedema, 70 Drugs 2171 (Year: 2010).

Hulpke-Wette, et al., "BMS-193884 and BMS-207940 Bristol-Myers Squibb" Current Opinion in Investigational Drugs (2002), 3(7), 1057-1061.

International Search Report and Written Opinion dated Feb. 3, 2021, for International Application No. PCT/US2020/058411 filed Oct. 30, 2020. (8 pages).

International Search Report of International Application No. PCT/US2021/016414 dated Apr. 15, 2021, 3 pages.

Rosenthal Rita et al., "Endothelin Antagonism as an Active Principle for Glaucoma Therapy." British Journal of Pharmacology (2011) 162, 806-816.

Sasaoka et al., "Intravitreal injection of endothelin-1 caused optic nerve damage following to ocular hypoperfusion in rabbits" Experimental Eye Research 83 (2006) 629-637.

Shoshani, et al., "Endothelin and its suspected role in the pathogenesis and possible treatment of glaucoma" Current Eye Research 37(1), 1-11, 2012.

Caira et al., "Crystalline Polymorphism of Organic Compounds", Topics in Current Chemistry; Spring Berlin, DE, vol. 198, Jan. 1, 1998, pp. 163-208.

Murugesan et al., "Biphenylsulfonamide Endothelin receptor Antagonists", Journal of Medicinal Chemistry, American Chemical Society, US, vol. 46, No. 1, Nov. 26, 2002, pp. 135-137.

COMPOSITIONS FOR TREATMENT OF OCULAR DISEASES

RELATED APPLICATIONS

This application is a continuation of International Application Number PCT/US2021/016414 filed on Feb. 3, 2021, which claims priority to U.S. Provisional Patent Application Nos. 62/971,002 and 63/010,212, respectively filed on Feb. 6, 2020 and Apr. 15, 2020; the entire contents of which are hereby incorporated by reference for all purposes.

FIELD

The present disclosure relates to the field of medicine and the treatment of ocular disease. More specifically, the present disclosure relates to the use of certain compositions comprising Edonentan crystalline forms in the treatment or amelioration of glaucoma, diabetic retinopathy (DR), retinal vein occlusion (RVO), and retinopathy of prematurity (ROP).

BACKGROUND

Diseases of the eye have an enormous impact on the quality of human life and yet remain largely elusive to effective treatment. It is estimated that an annual economic burden of over $100 billion results from vision loss, eye diseases, and vision disorders in the U.S. Examples of debilitating ocular diseases include glaucoma, diabetic retinopathy (DR), retinal vein occlusion (RVO), and retinopathy of prematurity (ROP).

Glaucoma is an eye disorder characterized by visual field defects and excavation of the optic nerve head. An abnormally high intraocular pressure is commonly known to be detrimental to the eye, and there are clear indications that, in glaucoma patients, this probably is the most important physical change causing degeneration of the retina. Ultimately, if untreated, there is gradual loss of vision over time. The pathophysiological mechanism of glaucoma is, however, still unknown.

There are three basic types of glaucoma: primary, secondary, and congenital. Primary glaucoma is the most common type and can be divided into open-angle and closed-angle glaucoma. Primary open angle glaucoma ("POAG"; e.g., normal tension glaucoma (NTG)) is the most frequent type of glaucoma observed in the United States. POAG is usually detected in its early stages during routine eye examinations. Primary closed angle glaucoma, also called acute glaucoma, usually has a sudden onset and is characterized by eye pain and blurred vision. Secondary glaucoma occurs as a complication of a variety of other conditions, such as pseudoexfoliation syndrome, injury, inflammation, generalized vascular disease, and diabetes. Congenital glaucoma is due to a developmental defect in the eye's drainage mechanism.

Diabetic retinopathy (DR) is the most common complication of diabetes and the leading cause of decreased visual acuity and blindness in working-age population in developed countries. The incidence of DR increases with the time of evolution of diabetes. Thus, 90% of patients with type 1 diabetes and 60% of patients with type 2 diabetes have some degree of DR after 20 years of evolution of diabetes. The prevalence of DR in Western countries is very similar and is around 30% and in 10% of cases the DR is in advanced stages that seriously threaten vision.

DR occurs when changes in blood glucose levels cause changes in retinal blood vessels. In some cases, these vessels will swell up (macular edema) and leak fluid into the rear of the eye. In other cases, abnormal blood vessels will grow on the surface of the retina. Unless treated, DR can gradually become more serious and progress from 'background retinopathy' to seriously affecting vision and can lead to blindness.

Retinal vein occlusion (RVO) is a vascular disorder of the retina and one of the most common causes of vision loss worldwide. Specifically, it is the second most common cause of blindness from retinal vascular disease after diabetic retinopathy. RVO is often the result of underlying health problems (e.g., high blood pressure, high cholesterol levels, diabetes, and other health problems). There are two types of retinal vein occlusion: central retinal vein occlusion (CRVO) is the blockage of the main retinal vein, and branch retinal vein occlusion (BRVO) is the blockage of one of the smaller branch veins.

Currently, there is no way to unblock retinal veins, and accepted treatments are directed to addressing health problems related to the retinal vein occlusion. Vision may come back in some eyes that have had a retinal vein occlusion. About ⅓ have some improvement, about ⅓ stay the same and about ⅓ gradually improve, but it can take a year or more to determine the final outcome. In some cases, the blocked vessels will lead to fluid accumulation in the retina. In other cases, occurrence of ischemia causes the formation of new blood vessels. RVO is currently treated with intravitreal injection of anti-VEGF drugs.

Retinopathy of prematurity (ROP) can occur due to premature birth. Abnormal, leaky blood vessel growth (neovascularization) in the retina occurs secondary to other treatments for prematurity and can often lead to neonatal blindness. During pregnancy, blood vessels grow from the center of a developing baby's retina 16 weeks into the mother's pregnancy, and then branch outward and reach the edges of the retina 8 months into the pregnancy. In babies born prematurely, normal retinal vessel growth is incomplete and may therefore be more readily disrupted.

Endothelins ("ETs") are a family of naturally occurring peptides identified as ET-1, ET-2, and ET-3. Produced primarily in the endothelial cells with a key role in vascular homeostasis, ETs constrict blood vessels and raise blood pressure in the kidney affecting glomerular hemodynamics, and sodium and water homeostasis. When over expressed, ETs contribute to high blood pressure (hypertension), heart disease, disorders in the kidney and potentially other diseases such as ocular diseases. See, e.g., Salvatore et al., J Ophthalmol. 2010, 2010: 354645.

An endothelin receptor antagonist is a pharmacological agent that inhibits endothelin receptor(s). Some agents inhibit both endothelin A receptor and endothelin B receptor, and others selectively inhibit one of the two receptors only (e.g., endothelin A receptor antagonist). Endothelin receptor antagonists have been shown to decrease mortality and improve hemodynamics in experimental models (e.g., heart failure).

Edonentan (BMS-207940) is a highly selective and very potent endothelin A receptor antagonist. Edonentan was developed as a second-generation analog following the discontinuation of the first clinical candidate, BMS-193884, which was being developed for the treatment of congestive heart failure (CHF). Edonentan was studied in phase I trials by April 2002, but its development was discontinued.

There remains a need to more effectively reduce the incidence of, treat or otherwise ameliorate glaucoma, DR, RVO, and ROP.

SUMMARY

The present invention provides a method of using certain compositions comprising Edonentan crystalline forms for treating an ocular disease selected from glaucoma, diabetic retinopathy (DR), retinal vein occlusion (RVO), and retinopathy of prematurity (ROP).

In one aspect, this invention relates to a solid form of a compound of Formula I:

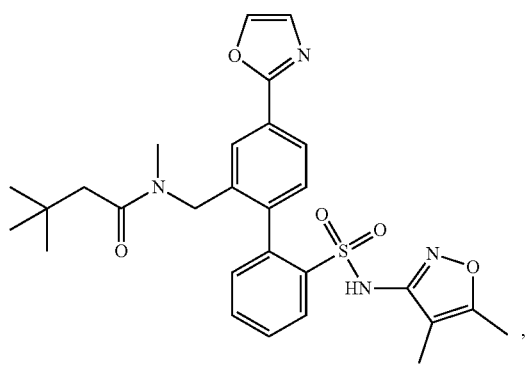

(I)

wherein said solid form is an anhydrous crystalline form (Form 4), having an X-ray powder diffraction pattern comprising at least three characterization peaks, in terms of 2θ, selected from peaks at 5.6±0.2°, 11.4±0.2°, 17.7±0.2°, 19.3±0.2°, 21.1±0.2°, and 21.9±0.2°.

In some embodiments of the solid form, the anhydrous crystalline Form 4 has the following X-ray powder diffraction pattern expressed in terms of diffraction angles (2θ): 5.6±0.2°, 11.4±0.2°, 17.7±0.2°, 19.3±0.2°, and 21.9±0.2°.

In some embodiments of the solid form, the anhydrous crystalline Form 4 has the following X-ray powder diffraction pattern expressed in terms of diffraction angles (2θ): 11.4±0.2°, 17.7±0.2°, and 19.3±0.2°.

In some embodiments of the solid form, the anhydrous crystalline Form 4 shows a $T_m$ of about 163° C. by DSC analysis.

In another aspect, this invention features a composition comprising a compound of Formula I:

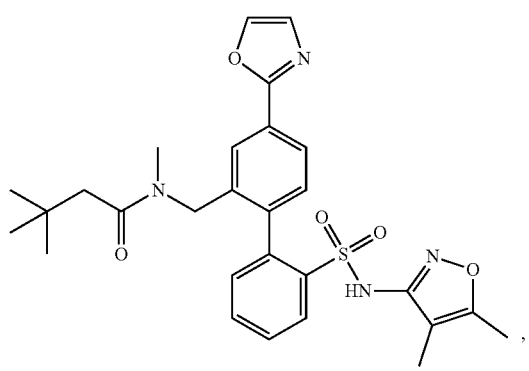

(I)

wherein said compound is an anhydrous crystalline form (Form 4), having an X-ray powder diffraction pattern comprising at least three characterization peaks, in terms of 2θ, selected from peaks at 5.6±0.2°, 11.4±0.2°, 17.7±0.2°, 19.3±0.2°, 21.1±0.2°, and 21.9±0.2°; and said compound is 90% by weight or more in crystalline Form 4 based on the total weight of the compound present in the composition.

In some embodiments, the compound of Formula I is 95% by weight or more in crystalline Form 4 based on the total weight of the compound present in the composition.

In some embodiments, the compound of Formula I is 96% by weight or more in crystalline Form 4 based on the total weight of the compound present in the composition.

In some embodiments, the compound of Formula I is 97% by weight or more in crystalline Form 4 based on the total weight of the compound present in the composition.

In some embodiments, the compound of Formula I is 98% by weight or more in crystalline Form 4 based on the total weight of the compound present in the composition.

In some embodiments, the compound of Formula I is 99% by weight or more in crystalline Form 4 based on the total weight of the compound present in the composition.

Still within the scope of this invention is a method of treating an ocular disease, comprising contacting an optical tissue in a subject with a composition containing a therapeutically effective amount of a compound of Formula I:

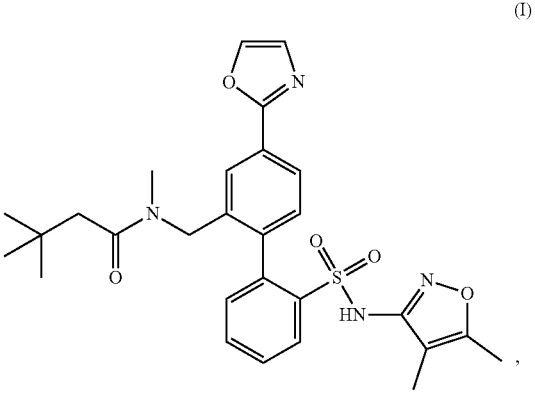 [SMILES: Cc1onc(NS(=O)(=O)c2ccccc2-c2ccc(-c3ncco3)cc2CN(C)C(=O)CC(C)(C)C)c1C]

(I)

le;2qwherein the ocular disease is selected from the group consisting of glaucoma, diabetic retinopathy (DR), retinal vein occlusion (RVO), and retinopathy of prematurity (ROP); said compound is a crystalline form (Form 4), wherein the crystalline Form 4 has an X-ray powder diffraction pattern comprising at least three characterization peaks, in terms of 2θ, selected from peaks at 5.6±0.2°, 11.4±0.2°, 17.7±0.2°, 19.3±0.2°, 21.1±0.2°, and 21.9±0.2°; and the compound is 90% by weight or more in crystalline Form 4 based on the total weight of the compound present in the composition.

This invention further covers a method of preparing an anhydrous crystalline form (Form 4) of a compound of Formula I:

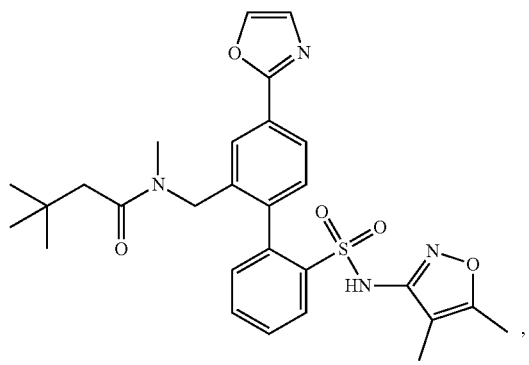

(I)

the method comprising:

(a) stirring the compound of Formula I in an aqueous solution, an organic solvent, or a mixture thereof, at a temperature in the range of about 40° C. to about 120° C.;

(b) cooling the resulting solution to a temperature in the range of about 0° C. to room temperature (e.g., about 25° C.) and, when the compound is in a basic aqueous solution, adjusting the pH value to the range of about 3 to about 7 (e.g., by the addition of HCl); and (c) filtering the sample thus obtained to afford crystalline Form 4, wherein said crystalline Form 4 has an X-ray powder diffraction pattern comprising at least three characterization peaks, in terms of 2θ, selected from peaks at 5.6±0.2°, 11.4±0.2°, 17.7±0.2°, 19.3±0.2°, 21.1±0.2°, and 21.9±0.2°.

In some embodiments of the preparation method, the aqueous solution is water.

In some embodiments of the preparation method, the aqueous solution is a basic aqueous solution. In some embodiments, the pH value of the basic aqueous solution is 8 or above.

In some embodiments of the preparation method, the basic aqueous solution is an aqueous potassium hydroxide or potassium carbonate solution.

In some embodiments of the preparation method, the organic solvent is a water-soluble organic solvent. In some embodiments, the organic solvent is tetrahydrofuran or isopropanol.

In some embodiments of the preparation method, the temperature for stirring is in the range of about 80° C. to about 120° C. (e.g., about 80° C. to about 90° C., about 90° C. to about 100° C., about 100° C. to about 110° C., or about 110° C. to about 120° C.).

In some embodiments of the preparation method, the temperature for stirring is in the range of about 40° C. to about 80° C. (e.g., about 40° C. to about 50° C., about 50° C. to about 60° C., about 60° C. to about 70° C., or about 70° C. to about 80° C.).

In some embodiments of the preparation method, the stirring takes place for about 20 hours to about 50 hours (e.g., about 20 hours to about 30 hours, about 30 hours to about 40 hours, or about 40 hours to about 50 hours).

In some embodiments of the preparation method, a slurry of the compound of Formula I is formed in the stirring step.

In some embodiments of the preparation method, the method further comprises seeding an amount of crystalline Form 4 and holding the resulting solution for about 2 hours.

In some embodiments of the preparation method, the cooling occurs at about 5° C. for about 15 hours.

In some embodiments of the preparation method, the pH value of the basic aqueous solution is adjusted to the range of about 3 to about 4. In some embodiments of the preparation method, the pH value of the basic aqueous solution is adjusted to the range of about 3 to about 5. In some embodiments of the preparation method, the pH value of the basic aqueous solution is adjusted to the range of about 3 to about 6. In some embodiments of the preparation method, the pH value of the basic aqueous solution is adjusted to the range of about 5 to about 6. In some embodiments of the preparation method, the pH value of the basic aqueous solution is adjusted to about 5.5 to about 6. In some embodiments of the preparation method, the pH value of the basic aqueous solution is adjusted to about 6 to about 7.

Also within the scope of this invention is a method of treating an ocular disease, comprising contacting an optical tissue in a subject with a composition containing a therapeutically effective amount of a compound of Formula I, i.e., Edonentan:

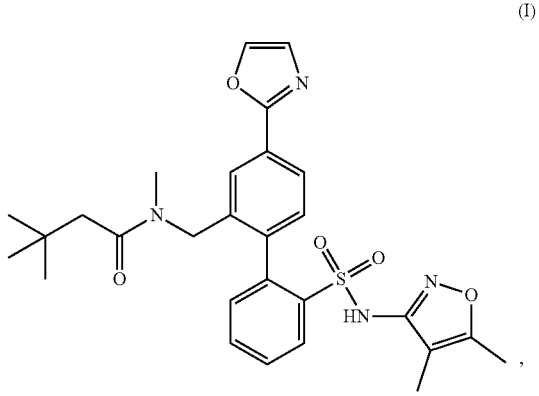 [SMILES: Cc1onc(NS(=O)(=O)c2ccccc2-c2ccc(-c3ncco3)cc2CN(C)C(=O)CC(C)(C)C)c1C]

(I)

wherein the ocular disease is selected from the group consisting of glaucoma, diabetic retinopathy (DR), retinal vein occlusion (RVO), and retinopathy of prematurity (ROP); said compound is selected from the group consisting of an anhydrous crystalline form (Form 1); a monohydrate crystalline form (Form 2); and an anhydrous crystalline form (Form 3), wherein:

(i) the anhydrous crystalline Form 1 has an X-ray powder diffraction pattern comprising at least three characterization peaks, in terms of 2θ, selected from peaks at 6.3±0.2°, 7.5±0.2°, 11.7±0.2°, 15.1±0.2°, and 17.3±0.2°; and said compound is 90% by weight or more in crystalline Form 1 based on the total weight of the compound present in the composition;

(ii) the monohydrate crystalline Form 2 has an X-ray powder diffraction pattern comprising at least three characterization peaks, in terms of 2θ, selected from peaks at 9.6±0.2°, 10.4±0.2°, 19.6±0.2°, 19.7±0.2°, 22.0±0.2°, 22.9±0.2°, and 23.7±0.2°; and said compound is 90% by weight or more in crystalline Form 2 based on the total weight of the compound present in the composition;

(iii) the anhydrous crystalline Form 3 has an X-ray powder diffraction pattern comprising at least three characterization peaks, in terms of 2θ, selected from peaks at 7.8±0.2°, 9.0±0.2°, 11.6±0.2°, 15.8±0.2°, and 19.1±0.2°; and said compound is 90% by weight or more in crystalline Form 3 based on the total weight of the compound present in the composition.

In some embodiments, contacting comprises administering a topical composition to a surface of an eye or a portion thereof. In other embodiments, contacting comprises injecting compositions containing Edonentan crystalline forms into an eye generally or in a specific area thereof.

In some embodiments, the ocular disease is glaucoma. In further embodiments, therapeutic efficacy in treating glaucoma is determined by detecting a reduction in intraocular pressure, or a reduction in the rate of optic nerve damage/retinal nerve fiber layer thinning, loss of contrast sensitivity or visual field, amount sufficient to relieve or prevent optic nerve damage. In other embodiments, therapeutic efficacy of treating glaucoma is determined by measuring an improvement in retinal, optic nerve head or tissue perfusion.

In some embodiments for the treatment of glaucoma, the regimen further comprises the addition of a therapeutically effective amount of an intra-ocular pressure (IOP) reducing agent or a neuroprotective agent, or a pharmaceutically acceptable salt of any of the foregoing. In some embodiments, the IOP reducing agent is selected from the group consisting of prostaglandins (such as latanoprost or travoprost), beta-blockers (such as timolol or betaxolol), alpha adrenergic agonists (such as brimonidine, apraclonidine), carbonic anhydrase inhibitors (such as dorzolamide or brinzolamide), Rho kinase inhibitors (such as netarsudil) and miotic or cholinergic agents (such as pilocarpine). In some embodiments, the neuroprotective agent is selected from the group consisting of anti-apoptotic agents (such as caspase-2 inhibitor) and neurotrophic factors (such as ciliary neurotrophic factor).

In some embodiments, the ocular disease is diabetic retinopathy (DR). In further embodiments, therapeutic efficacy of treating DR is determined by a decrease in retinal neovascularization, diabetic retinopathy severity score and neurodegeneration induced by diabetes. In other embodiments, therapeutic efficacy of treating DR is determined by measuring an improvement in retinal or choroid perfusion.

In some embodiments, the disease is retinal vein occlusion (RVO). In further embodiments, therapeutic efficacy of treating RVO is determined by measuring an improvement in tissue perfusion, a reduction in inflammation, or a combination of the foregoing.

In some embodiments, the ocular disease is retinopathy of prematurity (ROP). In further embodiments, therapeutic efficacy of treating ROP is determined by measuring an improvement in retinal perfusion and reduction in abnormal neovascularization.

In some embodiments, the administered composition contains an Edonentan crystalline form in a dosage between about 1 μg and about 5 mg (e.g., between about 1 μg and about 10 μg, between about 10 μg and about 50 μg, between about 50 μg and about 100 μg, between about 100 μg and about 500 μg, between about 500 μg and about 1 mg, between about 1 mg and about 1.5 mg, between about 1.5 mg and about 2 mg, between about 2 mg and 2.5 mg, between about 2.5 mg and about 3 mg, between about 3 mg and 3.5 mg, between about 3.5 mg and 4 mg, between about 4 mg and 4.5 mg, and between about 4.5 mg and 5 mg). In some embodiments, the administered composition contains an Edonentan crystalline form in a dosage between about 10 μg and about 3 mg (e.g. between about 10 μg and about 100 μg, between about 10 μg and about 500 μg, between about 10 μg and about 1 mg, between about 10 μg and about 2 mg, about 10 μg, about 25 μg, about 50 μg, about 75 μg, about 100 μg, about 125 μg, about 150 μg, about 175 μg, about 200 μg, about 250 μg, about 300 μg, about 350 μg, about 400 μg, about 450 μg, about 500 μg, about 550 μg, about 600 μg, about 650 μg, about 700 μg, about 750 μg, about 800 μg, about 850 μg, about 900 μg, about 950 μg, about 1 mg, about 1.25 mg, about 1.5 mg, about 1.75 mg, about 2 mg, about 2.25 mg, about 2.5 mg, about 2.75 mg, about 3 mg). In some embodiments, the administered composition contains an Edonentan crystalline form in a dosage between about 10 μg and about 1 mg. In some embodiments, the composition described herein is administered in a single dosage form. In some embodiments, the composition described herein is administered in multiple dosage forms.

This invention also covers a method of preparing a monohydrate crystalline form (Form 2) of a compound of Formula I:

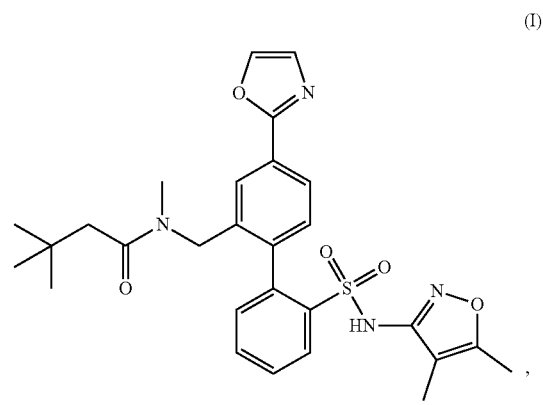 [SMILES: Cc1onc(NS(=O)(=O)c2ccccc2-c2ccc(-c3ncco3)cc2CN(C)C(=O)CC(C)(C)C)c1C]

(I)

the method comprising:

(a) preparing a slurry the compound of Formula I (e.g., amorphous form) in an aqueous medium (e.g., water) at a temperature in the range of about 15° C. to about 35° C. for a predetermined length of time (e.g., about 15 hours) to obtain a sample; and (b) filtering the sample thus obtained to afford crystalline Form 2, wherein said crystalline Form 2 has an X-ray powder diffraction pattern comprising at least three characterization peaks, in terms of 2θ, selected from peaks at 9.6±0.2°, 10.4±0.2°, 19.6±0.2°, 19.7±0.2°, 22.0±0.2°, 22.9±0.2°, and 23.7±0.2°.

In some embodiments of the preparation method, the aqueous medium is water.

In some embodiments of the preparation method, the predetermined length of time is about 15 hours.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof.

The details of one or more embodiments of the disclosure are set forth in the description below. Other features, objects, and advantages of the disclosure will be apparent from the below drawings, description and from the claims.

DETAILED DESCRIPTION

Figure 1:
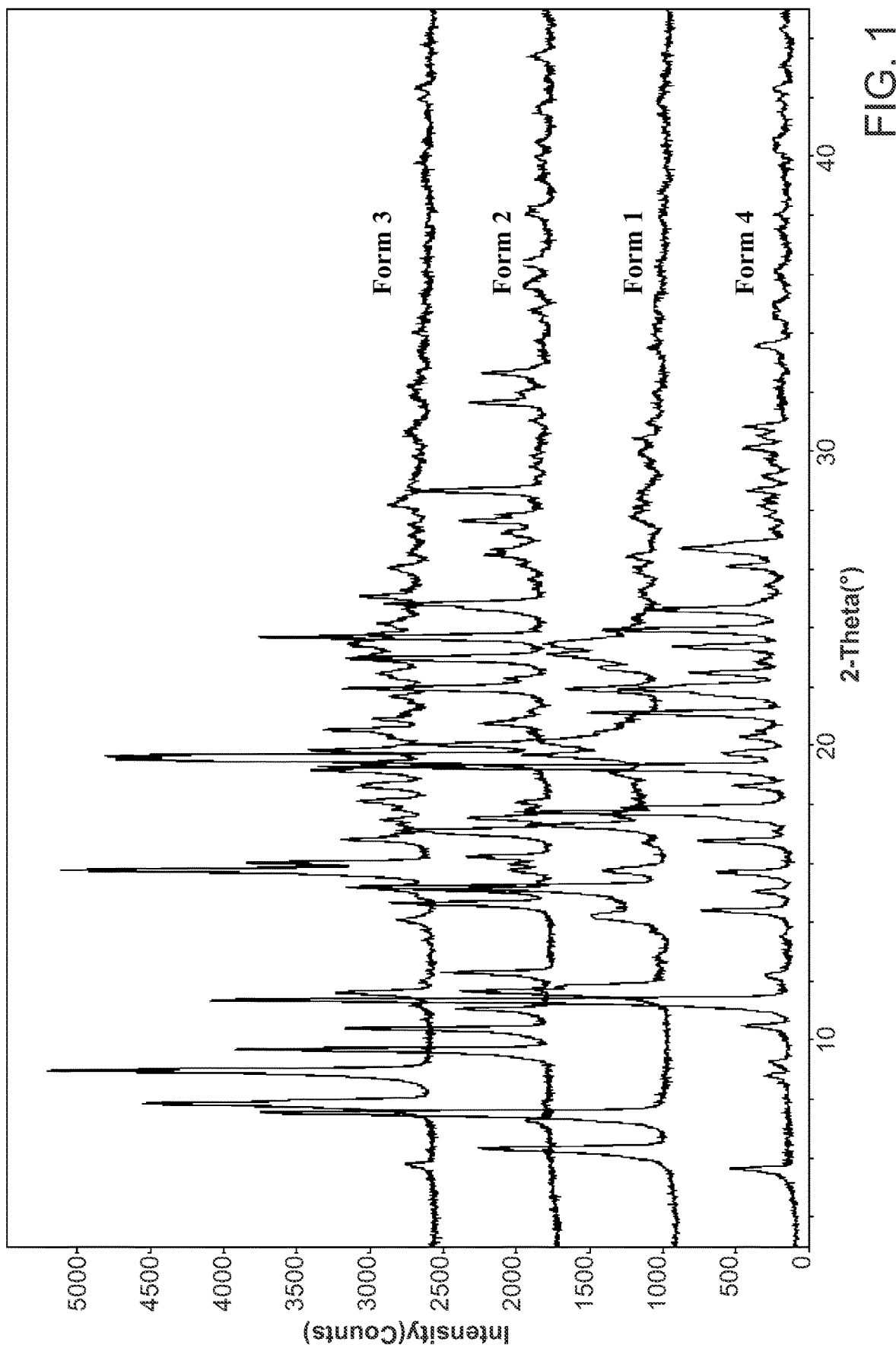
FIG. 1 depicts an exemplary XRPD pattern of Forms 1-4.

The present invention arises from the discovery that certain compositions comprising Edonentan crystalline forms can be used to prevent, treat or otherwise ameliorate ocular diseases including, but not limited to, glaucoma, diabetic retinopathy (DR), retinal vein occlusion (RVO), and retinopathy of prematurity (ROP). The invention is further described below.

As provided in the SUMMARY section, the present invention covers a method of treating an ocular disease, comprising contacting an optical tissue in a subject with a composition containing a therapeutically effective amount of a compound of Formula I above, wherein the ocular disease is selected from the group consisting of glaucoma, diabetic retinopathy (DR), retinal vein occlusion (RVO), and retinopathy of prematurity (ROP); the compound is an anhydrous crystalline form (Form 1), wherein the anhydrous crystalline Form 1 has an X-ray powder diffraction pattern comprising at least three characterization peaks, in terms of 2θ, selected from peaks at 6.3±0.2°, 7.5±0.2°, 11.7±0.2°, 15.1±0.2°, and 17.3±0.2°; and the compound is 90% by weight or more in crystalline Form 1 based on the total weight of the compound present in the composition.

In some embodiments, the anhydrous crystalline Form 1 has the following X-ray powder diffraction pattern expressed in terms of diffraction angles (2θ): 6.3±0.2°, 7.5±0.2°, 11.7±0.2°, and 15.1±0.2°.

In some embodiments, the anhydrous crystalline Form 1 has the following X-ray powder diffraction pattern expressed in terms of diffraction angles (2θ): 7.5±0.2°, 11.7±0.2°, and 15.1±0.2°.

In some embodiments, the anhydrous crystalline Form 1 has $T_m$ of about 151° C. by DSC analysis.

In some embodiments, the anhydrous crystalline Form 1 has a solubility of about 264 μg/mL at about pH 7 in a phosphate buffer.

In some embodiments, the compound of Formula I is 95% by weight or more in crystalline Form 1 based on the total weight of the compound present in the composition.

In some embodiments, the compound of Formula I is 96% by weight or more in crystalline Form 1 based on the total weight of the compound present in the composition.

In some embodiments, the compound of Formula I is 97% by weight or more in crystalline Form 1 based on the total weight of the compound present in the composition.

In some embodiments, the compound of Formula I is 98% by weight or more in crystalline Form 1 based on the total weight of the compound present in the composition.

In some embodiments, the compound of Formula I is 99% by weight or more in crystalline Form 1 based on the total weight of the compound present in the composition.

This invention also covers a method of treating an ocular disease, comprising contacting an optical tissue in a subject with a composition containing a therapeutically effective amount of a compound of Formula I, wherein the ocular disease is selected from the group consisting of glaucoma, diabetic retinopathy (DR), retinal vein occlusion (RVO), and retinopathy of prematurity (ROP); said compound is a monohydrate crystalline form (Form 2), wherein the monohydrate crystalline Form 2 has an X-ray powder diffraction pattern comprising at least three characterization peaks, in terms of 2θ, selected from peaks at 9.6±0.2°, 10.4±0.2°, 19.6±0.2°, 19.7±0.2°, 22.0±0.2°, 22.9±0.2°, and 23.7±0.2°; and the compound of Formula I is 90% by weight or more in crystalline Form 2 based on the total weight of the compound present in the composition.

In some embodiments, the monohydrate crystalline Form 2 has the following X-ray powder diffraction pattern expressed in terms of diffraction angles (2θ): 19.6±0.2°, 19.7±0.2°, and 9.6±0.2°.

In some embodiments, the monohydrate crystalline Form 2 has the following X-ray powder diffraction pattern expressed in terms of diffraction angles (2θ): 19.6±0.2°, 19.7±0.2°, 9.6±0.2°, 10.4±0.2°, 22.0±0.2°, and 22.9±0.2°.

In some embodiments, the monohydrate crystalline Form 2 has a $T_m$ of about 122° C. by DSC analysis.

In some embodiments, the monohydrate crystalline Form 2 has a solubility of about 35 μg/mL at about pH 7 in a phosphate buffer.

In some embodiments, the compound of Formula I is 95% by weight or more in crystalline Form 2 based on the total weight of the compound present in the composition.

In some embodiments, the compound of Formula I is 96% by weight or more in crystalline Form 2 based on the total weight of the compound present in the composition.

In some embodiments, the compound of Formula I is 97% by weight or more in crystalline Form 2 based on the total weight of the compound present in the composition.

In some embodiments, the compound of Formula I is 98% by weight or more in crystalline Form 2 based on the total weight of the compound present in the composition.

In some embodiments, the compound of Formula I is 99% by weight or more in crystalline Form 2 based on the total weight of the compound present in the composition.

This invention further covers a method of treating an ocular disease, comprising contacting an optical tissue in a subject with a composition containing a therapeutically effective amount of a compound of Formula I, wherein the ocular disease is selected from the group consisting of glaucoma, diabetic retinopathy (DR), retinal vein occlusion (RVO), and retinopathy of prematurity (ROP); said compound is an anhydrous crystalline form (Form 3), wherein the anhydrous crystalline Form 3 has an X-ray powder diffraction pattern comprising at least three characterization peaks, in terms of 2θ, selected from peaks at 7.8±0.2°, 9.0±0.2°, 11.6±0.2°, 15.8±0.2°, and 19.1±0.2°; and the compound of Formula I is 90% by weight or more in crystalline Form 3 based on the total weight of the compound present in the composition.

In some embodiments, the anhydrous crystalline Form 3 has the following X-ray powder diffraction pattern expressed in terms of diffraction angles (2θ): 9.0±0.2°, 15.8±0.2°, 7.8±0.2°, and 19.1±0.2°.

In some embodiments, the anhydrous crystalline Form 3 has the following X-ray powder diffraction pattern expressed in terms of diffraction angles (2θ): 9.0±0.2°, 15.8±0.2°, and 7.8±0.2°.

In some embodiments, the anhydrous crystalline Form 3 has a $T_m$ of about 162° C. by DSC analysis.

In some embodiments, the anhydrous crystalline Form 3 has a solubility of about 251 μg/mL at about pH 7 in a phosphate buffer.

In some embodiments, the compound of Formula I is 95% by weight or more in crystalline Form 3 based on the total weight of the compound present in the composition.

In some embodiments, the compound of Formula I is 96% by weight or more in crystalline Form 3 based on the total weight of the compound present in the composition.

In some embodiments, the compound of Formula I is 97% by weight or more in crystalline Form 3 based on the total weight of the compound present in the composition.

In some embodiments, the compound of Formula I is 98% by weight or more in crystalline Form 3 based on the total weight of the compound present in the composition.

In some embodiments, the compound of Formula I is 99% by weight or more in crystalline Form 3 based on the total weight of the compound present in the composition.

Still covered by this invention is a method of treating an ocular disease, comprising contacting an optical tissue in a subject with a composition containing a therapeutically effective amount of a compound of Formula I, wherein the ocular disease is selected from the group consisting of glaucoma, diabetic retinopathy (DR), retinal vein occlusion (RVO), and retinopathy of prematurity (ROP); said compound is a crystalline form (Form 4), wherein the crystalline Form 4 has an X-ray powder diffraction pattern comprising at least three characterization peaks, in terms of 2θ, selected from peaks at 5.6±0.2°, 11.4±0.2°, 17.7±0.2°, 19.3±0.2°, 21.1±0.2°, and 21.9±0.2°; and the compound of Formula I is 90% by weight or more in crystalline Form 4 based on the total weight of the compound present in the composition.

In some embodiments, the anhydrous crystalline Form 4 has the following X-ray powder diffraction pattern expressed in terms of diffraction angles (2θ): 5.6±0.2°, 11.4±0.2°, 17.7±0.2°, 19.3±0.2°, and 21.9±0.2°.

In some embodiments, the anhydrous crystalline Form 4 has the following X-ray powder diffraction pattern expressed in terms of diffraction angles (2θ): 11.4±0.2°, 17.7±0.2°, and 19.3±0.2°.

In some embodiments, the crystalline Form 4 has the following X-ray powder diffraction pattern expressed in terms of diffraction angle 2θ:

| Angle [2θ] |
| --- |
| 5.6 |
| 11.4 |
| 17.7 |
| 19.3 |
| 21.1 |
| 21.9 |

In some embodiments, the anhydrous crystalline Form 4 has a $T_m$ of about 163° C. by DSC analysis.

In some embodiments, the compound of Formula I is 95% by weight or more in crystalline Form 4 based on the total weight of the compound present in the composition.

In some embodiments, the compound of Formula I is 96% by weight or more in crystalline Form 4 based on the total weight of the compound present in the composition.

In some embodiments, the compound of Formula I is 97% by weight or more in crystalline Form 4 based on the total weight of the compound present in the composition.

In some embodiments, the compound of Formula I is 98% by weight or more in crystalline Form 4 based on the total weight of the compound present in the composition.

In some embodiments, the compound of Formula I is 99% by weight or more in crystalline Form 4 based on the total weight of the compound present in the composition.

In some embodiments, therapeutic efficacy of the above-described treatment is determined by (i) detecting a reduction in intraocular pressure, or a reduction in a rate of optic nerve damage, in an amount sufficient to relieve or prevent optic nerve damage; (ii) assessing a degree of improvement in visual acuity or visual field; (iii) measuring a decrease in retinal neurodegeneration induced by diabetes; (iv) measuring an improvement in tissue or retinal perfusion; or (v) measuring an improvement in tissue or retinal perfusion, a reduction in inflammation, or a combination thereof.

Methods of the present invention include contacting the eye tissue (topically or intra-ocularly) with or administration of a therapeutically effective amount of compositions comprising Edonentan crystalline forms.

Methods of preparing Edonentan (e.g., amorphous Edonentan) are well known to a person of skill in the art. Suitable methods are disclosed, for example, in U.S. Pat. No. 6,043,265, and International Publication No. 2002/32884. Edonentan has the chemical name of N-[[2'-[[(4,5-dimethyl-3-isoxazolyl)amino]sulfonyl]-4-(2-oxazolyl)[1,1'-biphenyl]-2-yl]methyl]-N,3,3-trimethylbutanamide (molecular weight of 536.6 g/mol) and the structure of Formula I shown above.

Edonentan Crystalline Forms

Crystalline forms of Edonentan disclosed herein may be substantially more stable compared to the amorphous form of Edonentan. For example, a disclosed crystalline form (e.g., Form 4), may be stored under practical and economical storage conditions, while retaining physical properties so that it may be manufactured into a dosage form. In another set of examples, a disclosed crystalline form (e.g., Form 1, Form 2, Form 3) are converted to disclosed crystalline form (e.g., Form 4). For example, heating a slurry of crystalline Form 1 in about 20 mL of a mixture of isopropanol and water (1:2) at 80° C. for 24 hours, and then cooling and filtering the sample obtained from the solution affords the crystalline Form 4. In another example, stirring the amorphous form of a compound of Formula I in 20 mL of water at 25° C. for 15 hours affords crystalline Form 2, and then subsequently heating crystalline Form 2 at 100° C. for 40 hours followed by filtration affords the crystalline Form 4. In yet another example, heating a slurry of the anhydrous crystalline Form 3 in 30 mL of water at 80° C. for 40 hours and then cooling and filtering the sample obtained from the solution affords the crystalline Form 4. In an embodiment, crystalline Form 4 is more stable (e.g., thermodynamically) than certain other crystalline forms. In an embodiment, crystalline Form 4 is more stable (e.g., thermodynamically) than a crystalline form selected from the group consisting of crystalline Form 1, crystalline Form 2 and crystalline Form 3. In an embodiment, a disclosed crystalline form may have improved chemical and/or physical stability when e.g., compounded in a pharmaceutical formulation, as compared to e.g., the amorphous form. In some embodiments, the crystalline form is crystalline Form 4.

As used herein, the term "amorphous" refers to a solid material having no long range order in the position of its molecules. Amorphous solids are generally supercooled liquids in which the molecules are arranged in a random manner so that there is no well-defined arrangement, e.g., molecular packing, and no long range order. Amorphous solids are generally isotropic, i.e. exhibit similar properties in all directions and do not have definite melting points. For example, an amorphous material is a solid material having no sharp characteristic crystalline peak(s) in its X-ray power diffraction (XRPD) pattern (i.e., is not crystalline as determined by XRPD). Instead, one or several broad peaks (e.g., halos) appear in its XRPD pattern.

Hydrate forms of crystalline Edonentan are contemplated, e.g., Edonentan·$(H_2O)_m$, where m is a fractional or whole number between about 0 and about 4 inclusive. For example, contemplated herein are anhydrate or monohydrate forms of crystalline Edonentan. In an embodiment, a disclosed crystalline form of Edonentan may have a water level of about 1 to 10% by weight (e.g., 3 to 9% or 5 to 8% by weight).

Provided below is a general method of preparing crystalline Form 1 or crystalline Form 2: Amorphous (crude) Edonentan is dissolved in isopropyl alcohol (IPA). The solution is filtered and the filter is washed with a small amount of IPA. The resulting solution is headed to 60° C. and warm water is added dropwise while stirring vigorously and the solution is stirred at the same temperature for 1-2 h. The solution is slowly cooled to room temperature to provide crystalline Form 1 or Form 2 depending on the ratio of IPA to water. Alternatively, in a preferred method, amorphous (crude) Edonentan is slurried in 20 mL of water at 25° C. for 15 hours and then filtered to afford the crystalline Form 2.

Provided below is a general method of preparing crystalline Form 3: Amorphous (crude) Edonentan is dissolved in ethyl acetate (EA). The resulting solution is filtered and heated to 50-60° C. Hexane is added dropwise while stirring vigorously. More EA is added to clarify the solution followed by stirring at the same temperature for 1-2 h. The solution is slowly cooled to room temperature to provide crystalline Form 3.

Provided below is a general method of preparing crystalline Form 4: Amorphous (crude) Edonentan is added to a mixture solvent of an organic solvent (e.g., tetrahydrofuran) and water. The resulting mixture is stirred at elevated temperature, cooled and filtered to give Form 4. Alternatively, amorphous Edonentan is dissolved in a basic aqueous solution (e.g., an aqueous potassium hydroxide or potassium carbonate solution). The resulting solution is heated to 50-60° C., filtered warm and acidified with an acid (e.g., HCl). The resulting mixture is then stirred, cooled and filtered to give Form 4. Alternatively, in a preferred method, amorphous (crude) Edonentan is dissolved in 8 mL of isopropanol at 60° C. The resulting solution is cooled to 57° C., and then a small crystal of the crystalline Form 4 is added. After 2 hours, the solution is cooled to 5° C., held for 15 hours, and filtered to afford the crystalline Form 4.

Ocular Diseases

The methods of the present disclosure include the use of compositions comprising Edonentan crystalline forms described above in the treatment and amelioration of an ocular disease selected from glaucoma, diabetic retinopathy (DR), retinal vein occlusion (RVO), and retinopathy of prematurity (ROP), which are described below.

Glaucoma

In the treatment of glaucoma using compositions comprising Edonentan crystalline forms described herein, a "therapeutically effective amount" can be determined by assessing an improvement in retinal blood flow (RBF) over what could be achieved by the standard of care (lowering of intra-ocular pressure (TOP)). For a glaucoma indication, the improvement in blood flow in the healthy rabbit ocular model can be used as predictive of pharmacodynamic response (PD) in humans. Rabbits are commonly used to assess ocular PK/PD relationship for compounds targeting human ocular diseases due to the anatomic and functional similarities of the rabbit and human eye. Previously, intravitreal administration of ET-1 into the rabbit eye has been shown to induce significant vasoconstriction and optic nerve damage (Sasaoka M. et al, Exp Eye Res 2006; Sugiyama T. et al, Arch Ophthalmol 2009). Pharmacodynamic response in this model based on the reversal of perfusion impairment induced by intravitreal ET-1 administration, can be modeled for target pharmacodynamic response in human glaucoma patients where ET-1 levels are observed to be elevated in plasma and aqueous humor (Li S. et al, Journal of Ophthalmology 2016).

Other examples of relevant animal glaucoma models are Morrison's rat model of chronically elevated IOP and the laser-induced non-human primate (NHP) glaucoma model. Glaucoma in Morrison's rat model is induced by sustained elevation of IOP through hypertonic saline administration via episcleral veins. In a laser-induced NHP glaucoma model, after sustained elevation of IOP, optic nerve head blood flow has been shown to be reduced (Wang L. et al, Invest Ophthalmol Vis Sci 2012). Furthermore, the reduction in optic nerve head blood flow has been shown to correlate with long-term structural changes in the optic nerve (Cull G. et al, Invest Ophthalmol Vis Sci 2013). Edonentan is able to improve optic nerve head blood flow in a dose-dependent manner in the laser-induced NHP glaucoma model.

Efficacy in the above-described glaucoma models is defined as reduction in IOP, improvement in optic nerve head or retinal blood flow from baseline, prevention or slowing of the progression of structural neurodegenerative changes such as retinal nerve fiber layer thickness as measured by optical coherence tomography (OCT) or retinal ganglion cell counts on flat mount as well as functional changes such as electroretinography (ERG) or contrast sensitivity after treatment with a composition containing Edonentan crystalline forms.

It is believed that the effect of compositions comprising Edonentan crystalline forms on retinal blood flow can be assessed by the blood vessel radius (r) in Poiseuille's Law. An increase in (r) with an endothelin antagonist, would induce a more pronounced increase in blood flow than what can be achieved by an increase in perfusion pressure through IOP reduction:

$$\text{Blood flow} = (\text{perfusion pressure} \times \pi r^4)/(8\eta l)$$

where
l: blood vessel length
r: blood vessel radius
η: blood viscosity
perfusion pressure: mean arterial pressure—IOP Furthermore, compositions comprising Edonentan crystalline forms may reduce IOP and/or prevent RGC death through mechanisms independent of improvement in retinal/optic nerve head tissue perfusion. Accordingly, by using compositions containing certain specific Edonentan crystalline forms (e.g., Form 4), one (r) and/or more (TOP) of the above parameters can be altered to improve the RBF, thereby achieving therapeutic efficacy in treating glaucoma.

In some embodiments, the glaucoma patients are started on treatment as soon as they are diagnosed. In some embodiments, a composition comprising an Edonentan crystalline form is administered locally to the back of the eye using an intravitreal, suprachoroidal, or implant delivery platform with a frequency of every 3 to 12 (e.g., every 3 to 6 or every 4 to 6) months. In some embodiments of treating glaucoma, a composition comprising an Edonentan crystalline form is administered in topical form (e.g., eye drop).

Diabetic Retinopathy (DR)

Diabetes can cause serious late complications which are classified as microangiopathic (retinopathy, neuropathy and diabetic nephropathy) and macroangiopathic (cardiovascular disease). Diabetic retinopathy is the result of damage to the small blood vessels and neurons of the retina. The earliest changes leading to diabetic retinopathy include narrowing of the retinal arteries associated with reduced retinal blood flow; dysfunction of the neurons of the inner retina, followed in later stages by changes in the function of the outer retina, associated with subtle changes in visual function; dysfunction of the blood-retinal barrier, which protects the retina from many substances in the blood (including toxins and immune cells), leading to the leakage of blood constituents into the retinal neuropile. Later, the basement membrane of the retinal blood vessels thickens, capillaries degenerate and lose cells, particularly pericytes and vascular smooth muscle cells. This leads to loss of blood flow and progressive ischemia, and microscopic aneurysms which appear as balloon-like structures jutting out from the capillary walls, which recruit inflammatory cells; and lead to advanced dysfunction and degeneration of the neurons and glial cells of the retina.

Ischemia and oxidant injury observed in DR compromises blood flow and tissue ischemia which we have discovered can be reversed by compositions comprising Edonentan crystalline forms. For DR indication, the improvement in retinal perfusion is anticipated to reduce hypoxia and suppress vascular endothelial growth factor (VEGF) upregulation with a resultant benefit of slowing vascular proliferative changes, neovascularization and/or macular edema complications.

As a surrogate model for the ischemic retinopathy changes observed in DR, a preclinical mouse model of retinopathy of prematurity (ROP) can be used. Oxygen-induced retinopathy in the mouse is a reproducible and quantifiable proliferative retinal neovascularization model suitable for examining pathogenesis and therapeutic intervention for retinal neovascularization in ROP and other vasculopathologies including DR. The model is induced by exposure of one-week-old C57BL/6J mice to 75% oxygen for 5 days and then to room air as previously described (Smith L E H et al., Invest Ophthalmol Vis Sci 1994). Efficacy in this preclinical model of ROP can be assessed by studying retinal hypoxia and neovascularization. The current standard of care in DR includes anti-VEGF therapies which only address advanced vascular complications of disease. In some embodiments, the patients with DR are started on this treatment during the non-proliferative stages of the disease. In some embodiments, a composition comprising an Edonentan crystalline form is administered locally to the back of the eye using an intravitreal, suprachoroidal, or implant delivery platform with a frequency of every 3 to 12 (e.g., every 3 to 6 or every 4 to 6) months. In some embodiments of treating DR, a composition comprising an Edonentan crystalline form is administered in topical form (e.g., eye drop).

Retinal Vein Occlusion (RVO)

Retinal vein occlusion (RVO), a vascular disorder of the retina, is currently treated with intravitreal injection of anti-VEGF drugs to inhibit the growth factor that causes macular edema and corticosteroids to combat the inflammatory components which lead to edema. It is highly desirable to use compositions comprising Edonentan crystalline forms for treating RVO by improving tissue perfusion and reducing inflammation while avoiding the unwanted effects of systemic immunosuppression and/or local adverse effects of steroids.

RVO is currently treated with intravitreal steroids and anti-VEGF agents. We hypothesize that improving perfusion of existing vessels will reduce the degree of macular edema and VEGF upregulation and the downstream maladaptive changes that manifests as RVO. To test efficacy, a preclinical mouse model of ischemic retinopathy can be used. Oxygen-induced retinopathy in the mouse is a reproducible and quantifiable proliferative retinal neovascularization model suitable for examining pathogenesis and therapeutic intervention for retinal neovascularization in many ischemic retinopathies including RVO. The model is induced by exposure of one-week-old C57BL/6J mice to 75% oxygen for 5 days and then to room air as previously described (Smith L E H et al., Invest Ophthalmol Vis Sci 1994). The efficacy in this preclinical model of ischemic retinopathy can be assessed by studying retinal hypoxia and neovascularization. A "therapeutically effective amount" of a composition comprising an Edonentan crystalline form described herein can be additive to the current standard of care by improving tissue perfusion and reducing inflammation mediated by ET-1 while avoiding the unwanted effects of local steroids. In some embodiments of treating RVO, the composition comprising an Edonentan crystalline form is administered locally to the back of the eye using an intravitreal, suprachoroidal, or implant delivery platform. The frequency of administration will vary based on a patient's disease course and response to therapy. In some embodiments of treating RVO, a composition comprising an Edonentan crystalline form is administered in topical form (e.g., eye drop).

Retinopathy of Prematurity (ROP)

Retinopathy of prematurity (ROP) is a retinal vasoproliferative disease that affects premature infants. ROP continues to be a major preventable cause of blindness and visual handicaps globally. With improved perinatal care, improved survival of moderately preterm infants, and limited resources for oxygen delivery and monitoring, more mature preterm infants are developing severe ROP in developing countries.

The pathophysiology of ROP is characterized by two phases. Phase I ROP is due to vaso-obliteration beginning immediately after birth secondary to a marked decrease in vascular endothelial growth factor (VEGF) and insulin-like growth factor-1 (IGF-1). Phase II begins around 33 weeks' postmenstrual age (PMA). During this phase, VEGF levels increase, especially if there is retinal hypoxia with increasing retinal metabolism and demand for oxygen leading to abnormal vasoproliferation. For advanced stages of ROP, laser ablation of avascular retina, early treatment of ROP (ETROP) protocol, intravitreal injection of anti-VEGF antibodies (e.g. bevacizumab) and vitrectomy are used to protect central vision and prevent retinal detachment. Long-term complications such as refractory errors, recurrence of ROP and risk of retinal detachment require continued follow-up with an ophthalmologist through adolescence and beyond.

ROP is induced by severe ischemia due to underdevelopment of retinal vessels secondary to premature birth. Therefore, as an aspect of the invention, it is believed that improving perfusion of existing vessels with compositions comprising Edonentan crystalline forms will reduce the degree of ischemia and VEGF upregulation and the downstream maladaptive changes that manifests as ROP. To test efficacy, a preclinical mouse model of ROP may be used. Oxygen-induced retinopathy in the mouse is a reproducible and quantifiable proliferative retinal neovascularization model suitable for examining pathogenesis and therapeutic intervention for retinal neovascularization in ROP. The model is induced by exposure of one-week-old C57BL/6J mice to 75% oxygen for 5 days and then to room air as previously described (Smith L E H et al., Invest Ophthalmol Vis Sci 1994). The efficacy in this preclinical model of ROP can be assessed by studying retinal hypoxia and neovascularization. A "therapeutically effective amount" of a composition comprising an Edonentan crystalline form, as described herein will be additive to the current standard of care by improving tissue perfusion and reducing pathologic neovascularization induced by VEGF. In some embodiments, the medication is administered locally to the back of the eye using an intravitreal, suprachoroidal, or implant delivery platform with a frequency of every 4 to 6 weeks as needed based on patient's disease course and response to therapy. For example, the medication is administered locally to the back of the eye using an intravitreal injection with a frequency of every 5 weeks as needed based on patient's disease course and response to therapy. In some embodiments of treating ROP, a composition comprising an Edonentan crystalline form is administered in topical form (e.g., eye drop).

Pharmaceutical Compositions

Some embodiments described herein relates to a pharmaceutical composition, that can include (e.g., prepared from) a therapeutically effective amount of an Edonentan crystalline form, described herein, and a pharmaceutically acceptable carrier, diluent, excipient or combination thereof.

The term "pharmaceutical composition" refers to a mixture of one or both compounds disclosed herein with other chemical components, such as diluents or carriers. The pharmaceutical composition facilitates administration of the compound to an organism. Pharmaceutical compositions will generally be tailored to the specific intended route of administration.

The term "pharmaceutically acceptable" defines a carrier, diluent, excipient, salt or composition that is safe and effective for its intended use and possesses the desired biological and pharmacological activity.

As used herein, a "carrier" refers to a compound that facilitates the incorporation of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

As used herein, an "excipient" refers to an inert substance that is added to a pharmaceutical composition to provide, without limitation, bulk, consistency, stability, binding ability, lubrication, disintegrating ability, retarded dissolution etc., to the composition. A "diluent" is a type of excipient.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The pharmaceutical compositions described herein can be administered to a human patient per se, or in pharmaceutical compositions where they are mixed with other active ingredients, as in combination therapy, or carriers, diluents, excipients or combinations thereof. Proper formulation is dependent upon the route of administration chosen. Techniques for formulation and administration of the compounds described herein are known to those skilled in the art.

The pharmaceutical compositions disclosed herein may be manufactured in a manner that is itself known, e.g., by means of conventional mixing, dissolving, granulating, levigating, emulsifying, encapsulating or entrapping processes. See, e.g., Encapsulation Processes, in: Food Powders, 2005, 199-299. Additionally, the active ingredients are contained in an amount effective to achieve its intended purpose. Compounds used in the pharmaceutical combinations disclosed herein may be provided as pharmaceutically acceptable salts.

It is preferred to administer the compounds or pharmaceutical compositions of this invention in a local manner either as a topical ophthalmic formulation or via injection of the compounds or pharmaceutical compositions directly to the ocular tissue, often in a depot or sustained release formulation. The manner of local administration can be intravitreal, suprachoroidal, periocular, or subconjunctival injection of a formulation, or use of an implant technology or topical application. For example, the compound is administered in a liposomal preparation that slowly releases the compound sustaining the desired pharmacological effects. Alternatively, polyvinyl alcohol nanoparticles can be prepared by well-known methods to afford a sustained or extended release-formulation for topical or intra-ocular application.

In some embodiments, the pharmaceutical composition is an ophthalmic preparation comprising a therapeutically effective amount of a composition comprising an Edonentan crystalline form described herein. As used herein, an "ophthalmic preparation" refers to a specialized dosage form designed to be instilled onto the external surface of the eye (topical), administered inside (intraocular) or adjacent (periocular) to the eye or used in conjunction with an ophthalmic device. In some embodiments, the ophthalmic preparation is in the form of a solution, suspension, or an ointment. In other embodiments, the ophthalmic preparation is in the form of a gel, a gel-forming solution, an ocular insert, a micro/nanoparticle preparations for topical or preferably intravitreal injection, or an implant.

In some embodiments, the ophthalmic preparation comprises a preservative. Examples of suitable preservatives include, but are not limited to, cationic wetting agents (e.g, benzalkonium chloride), organic mercurials (e.g., phenylmercuric nitrate, phenylmercuric acetate), organic acids or their esters (e.g., sorbic acid, esters of p-hydroxybenzoic acid such as methyl hydroxybenzoate, propylhydroxybenzoate), and alcohol substitutes (e.g., chlorobutanol, phenylethanol). The preservative can be present in the ophthalmic preparation in an amount in the range of about 0.002% w/v to about 0.5% w/v (e.g., 0.01-0.25% w/v). The ophthalmic preparation can further comprise a preservative aid. Examples of suitable preservative aid include, but are not limited to, ethylenediaminetetraacetic acid (EDTA).

In some embodiments, the ophthalmic preparation comprises one or more additional excipients or agents to impart viscosity or lubrication, stabilize the active ingredients against decomposition, increase solubility of an active or inactive ingredient, adjust tonicity, or act as solvent. Examples of excipients or agents for imparting viscosity or lubrication include hypromellose, carbomer 974P, hydroxyethyl cellulose (HEC), polyvinyl alcohol, sodium hyaluronate, sodium carboxymethyl cellulose, Carbopol 940, hydroxypropylmethyl cellulose (HPMC), poloxamer, xyloglucan, alginic acid, sodium alginate, gellan gum, cellulose acetate phthalate, and xantham gum. Examples of excipients or agents as stabilizers include sodium bisulfite, sodium metabisulfite, sodium thiosulfate, and sodium sulfate/sulfuric acid, which can act as antioxidants. Examples of excipients or agents as solubilizers include providone, glycerol, polyethylene glycol (PEG), polypropylene glycol (PPG), PEG-stearate, poloxamer 407, tyloxapol, polysorbate 80, creatinine, cyclodextrin, and castor oil. Examples of excipients or agents for adjusting tonicity include sodium chloride, potassium chloride, calcium chloride dehydrate, magnesium chloride hexahydrate, sugars (e.g., sucrose, maltose, dextrose, etc.), glycerin, propylene glycol, mannitol, ascorbic acid, and acetylcysteine.

In some embodiments, the ophthalmic preparation comprises one or more buffers to adjust pH. Examples of buffers for adjusting pH include, but are not limited to, sodium citrate, monobasic sodium phosphate, dibasic sodium phosphate, boric acid, hepatahydrate, sodium acetate trihydrate, sodium citrate dihydrate, histidine, and phosphate buffered saline (PBS). The resulting composition can have a pH value of 5.0-8.5 (e.g., 5.0-6.0, 5.2-5.8, 6.0-8.0, 6.6-7.8, 6.2-8.2, and 6.2-7.5)

In some embodiments, the ophthalmic preparation comprises one or more surfactants. Examples of surfactants include sorbitan ether esters of oleic acid (e.g., polysorbate or Tween 20 and 80) and tyloxapol.

The volume that can be injected to a human eye at one time is around 50-90 μL through the intravitreal route, up to 450 μL through a subretinal route, and up to 200 μL via suprachoroidal routes. The needle used in these routes is typically 27 to 30 G in size. The dose depends on the concentration that can be formulated to fit this volume, potency, target efficacy and pharmacokinetic profile for each indication. Generally, the injections to the eye will not be administered at a frequency greater than once per month per eye. In some embodiments, when a composition of this invention is administered in topical form (i.e., eye drop), the volume administered to a human eye at one time can be around 50 μL (the concentration of the eye drop can be about 5 mg/mL).

In some embodiments, the intravitreal formulation will comprise a dose of a composition comprising an Edonentan crystalline form in the range of about 1 μg to about 1 mg. A first exemplary formulation comprises about 1 μg to about 1 mg of a composition comprising an Edonentan crystalline form described above, about 10 mM histidine HCl, about 10% α,α-trehalose dihydrate, and about 0.01% polysorbate 20. A second exemplary formulation comprises about 1 μg to about 1 mg of a composition comprising an Edonentan crystalline form, about 10 mM sodium phosphate, about 40 mM sodium chloride, about 0.03% polysorbate 20, and about 5% sucrose.

Without further elaboration, it is believed that one skilled in the art can, based on the above description, utilize the present invention to its fullest extent. The following specific examples are therefore to be construed as merely illustrative, and not limitative of the remainder of the disclosure in any way whatsoever.

EXAMPLES

In order that the invention described herein may be more fully understood, the following examples are set forth. The examples described in this application are offered to illustrate the aspects of the invention and their embodiments provided herein and are not to be construed in any way as limiting their scope.

The compounds subject to crystallization provided herein can be prepared from readily available starting materials using known procedures. The compounds can be crystallized using the procedures described herein.

Abbreviations

DSC differential scanning calorimetry
EA ethyl acetate
IPA isopropyl alcohol
PBS phosphate-buffered saline
XRPD X-ray powder diffraction Example 1: Exemplary Method of Preparing Crystalline Form 1

Figure 2:
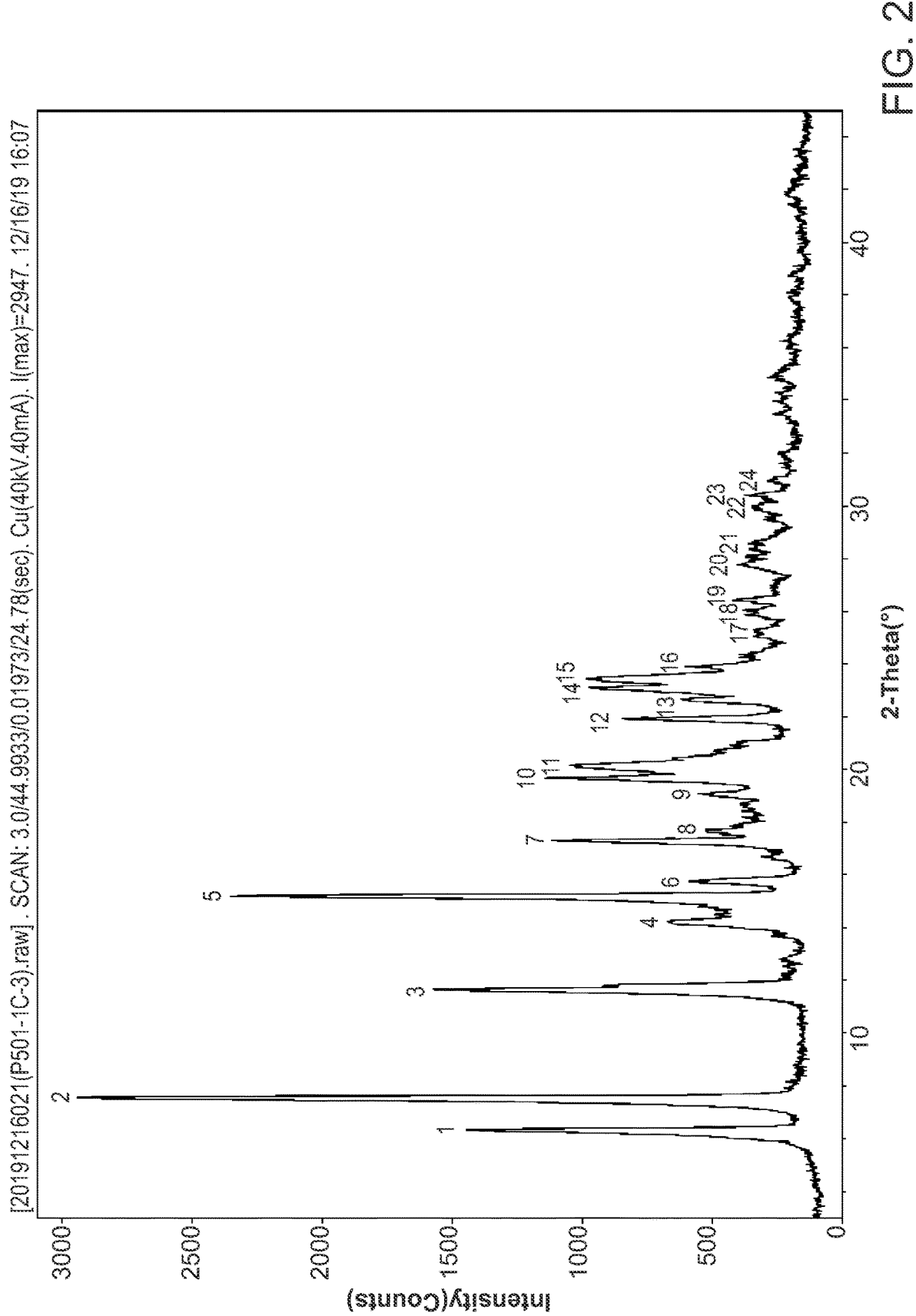
FIG. 2 depicts an exemplary XRPD pattern of Form 1.
Figure 6:
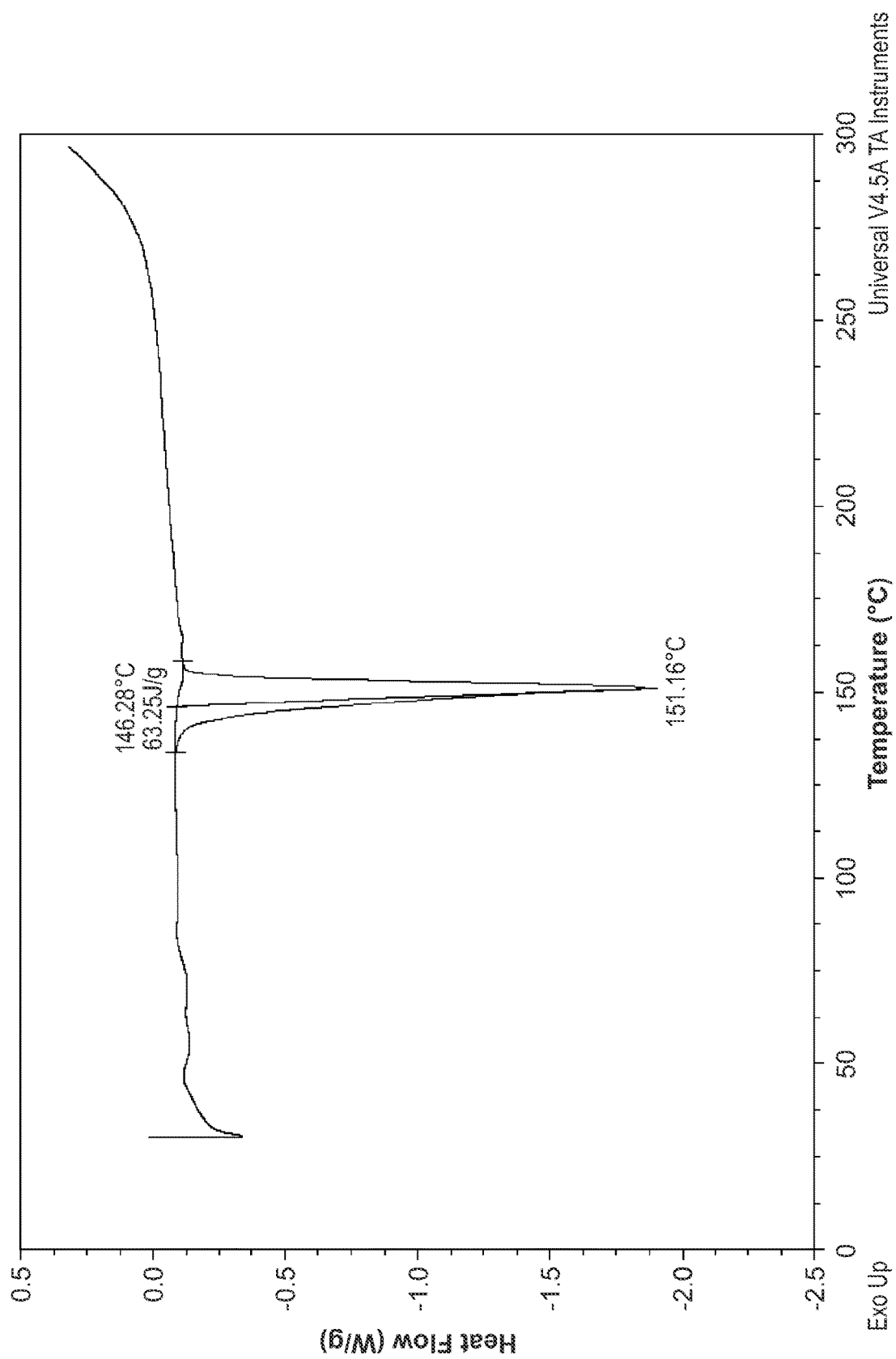
FIG. 6 depicts an exemplary DSC curve of Form 1.

Amorphous Edonentan (840 mg) was dissolved in 12 mL of IPA. The resulting solution was filtered and the filter was washed with additional 2.5 mL of IPA. The filtrated was concentrated to dryness, dissolved in 11.8 mL of IPA and heated with stirring to 60° C. Then, 18 mL of warm water was added dropwise at 60° C. while stirring vigorously and the solution was stirred at 60° C. for 1 h. The solution was slowly cooled to 25° C., filtered and dried under vacuum at 25° C. to provide 660 mg of crystalline Form 1 (XRPD and DSC in FIG. 2 and FIG. 6, respectively).

Example 2: Exemplary Method of Preparing Crystalline Form 2

Figure 3:
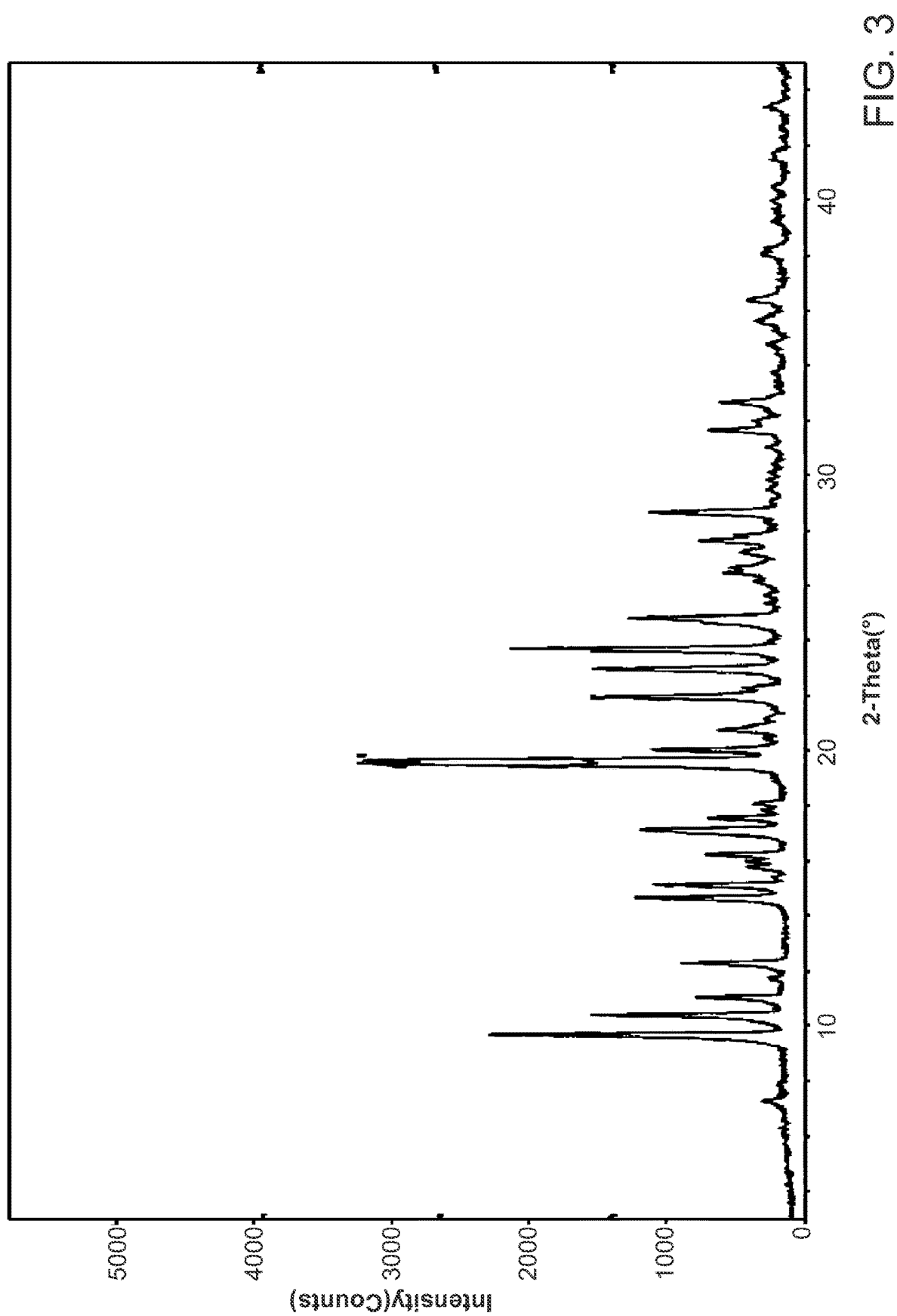
FIG. 3 depicts an exemplary XRPD pattern of Form 2.
Figure 7:
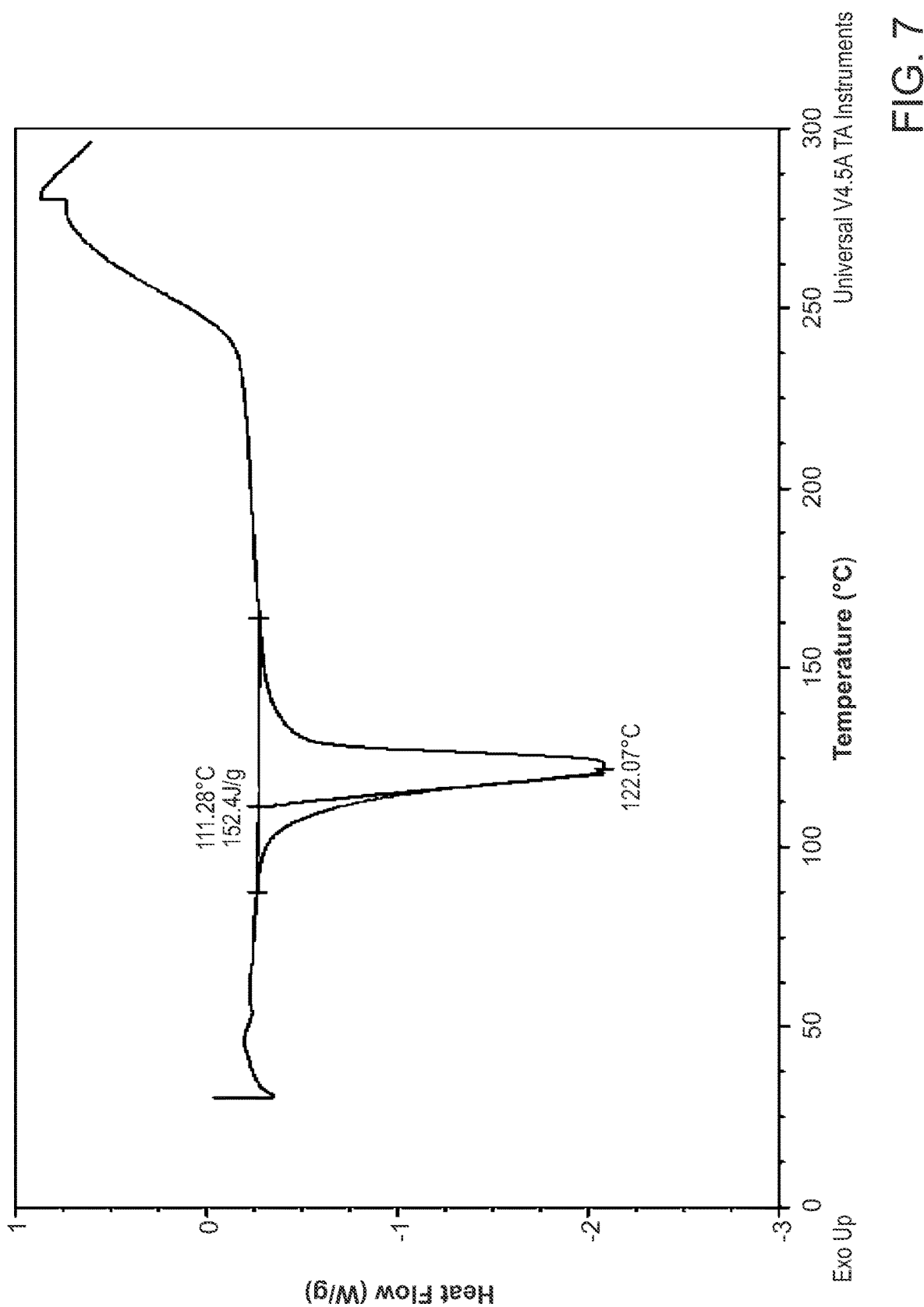
FIG. 7 depicts an exemplary DSC curve of Form 2.

Amorphous Edonentan (250 mg) was dissolved in 3.5 mL of IPA. The resulting solution was filtered and the filter was washed with additional 0.25 mL of IPA. The solution was then heated to 60° C. whereupon 7.5 mL of warm water was added dropwise at 60° C. while stirring vigorously and then stirred at 60° C. for 1 h. After slowly cooling to 25° C., the mixture was filtered to provide crystalline Form 2 (XRPD and DSC in FIG. 3 and FIG. 7, respectively).

Alternatively, a preferred method of preparing crystalline Form 2 is as follows. Amorphous Edonentan (1 g) was slurried in 20 mL of water at 25° C. for 15 hours. The solution was then filtered to give the crystalline Form 2 (XRPD and DSC in FIG. 3 and FIG. 7, respectively).

Example 3: Exemplary Method of Preparing Crystalline Form 3

Figure 4:
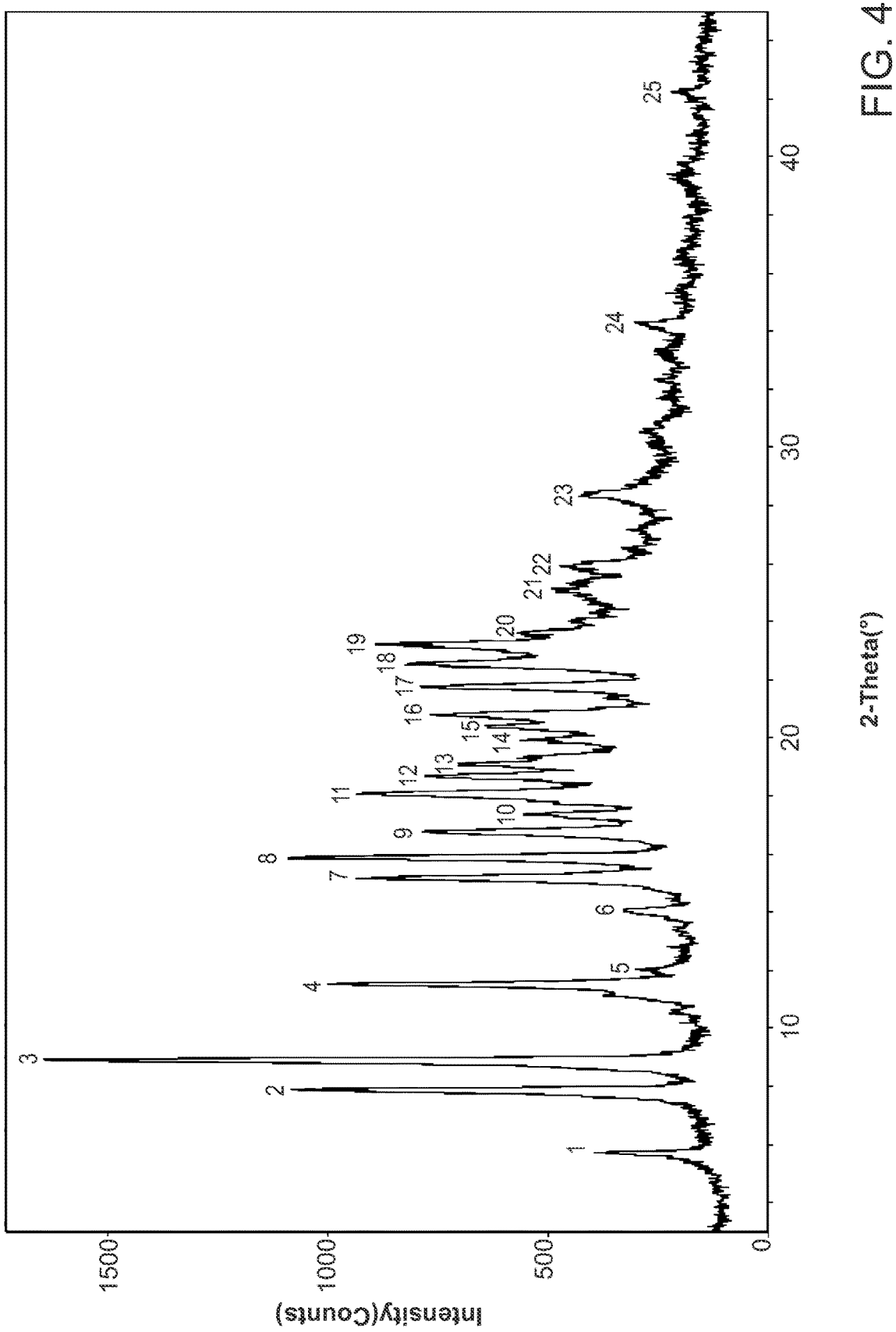
FIG. 4 depicts an exemplary XRPD pattern of Form 3.
Figure 8:
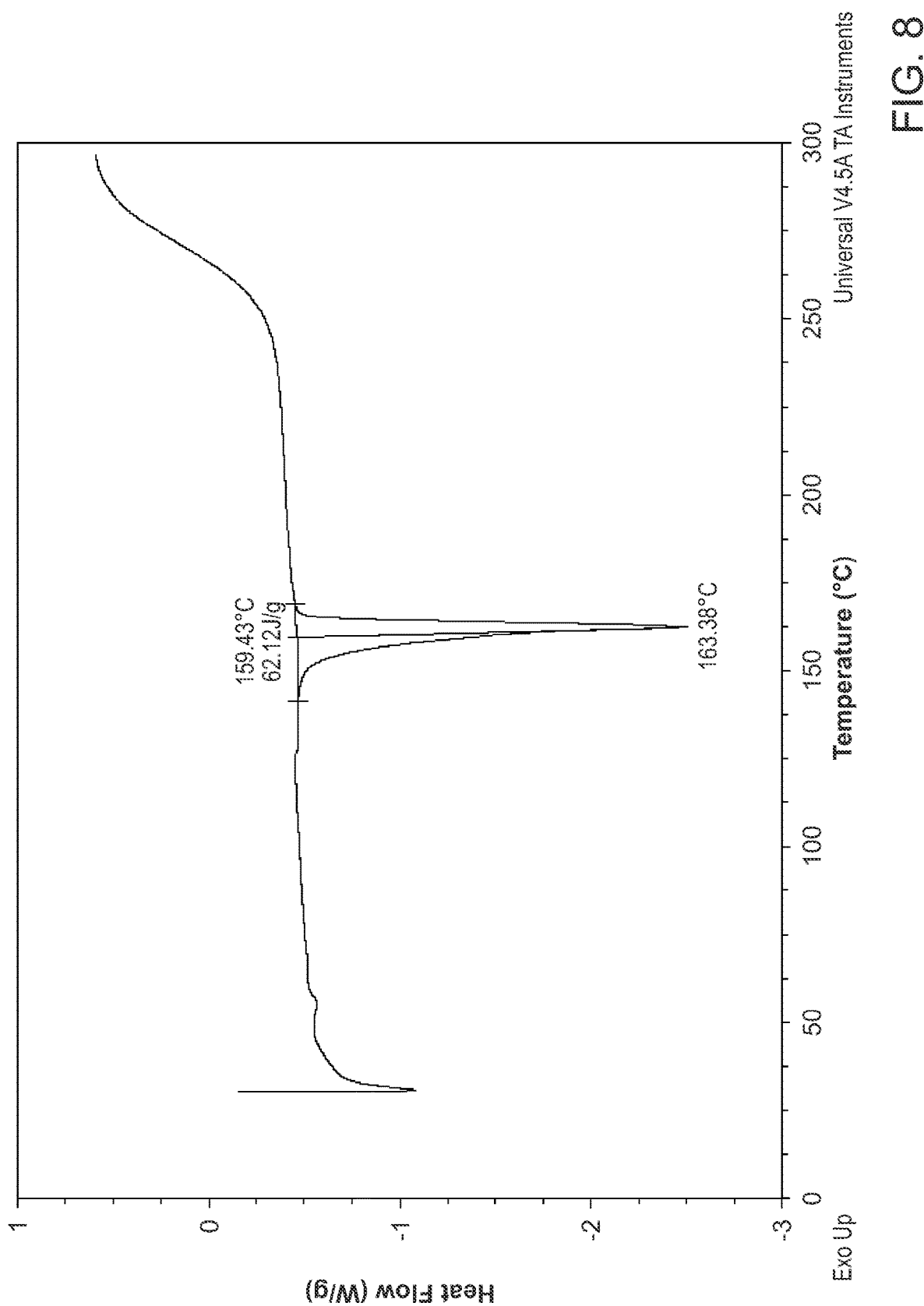
FIG. 8 depicts an exemplary DSC curve of Form 3.

Amorphous Edonentan (250 mg) was dissolved in 0.5 mL of ethyl acetate. The resulting solution was filtered and heated to 60° C., and 1.5 mL of hexane was added dropwise at 60° C. while stirring vigorously. To the resulting slightly cloudy solution, 0.1 mL of ethyl acetate was added, resulting in a clear solution which was then stirred at 60° C. for 1 h. The solution was slowly cooled to 25° C. and the resulting precipitate was filtered to provide crystalline Form 3 (XRPD and DSC in FIG. 4 and FIG. 8, respectively).

Example 4: Exemplary Methods of Preparing Crystalline Form 4

Figure 9:
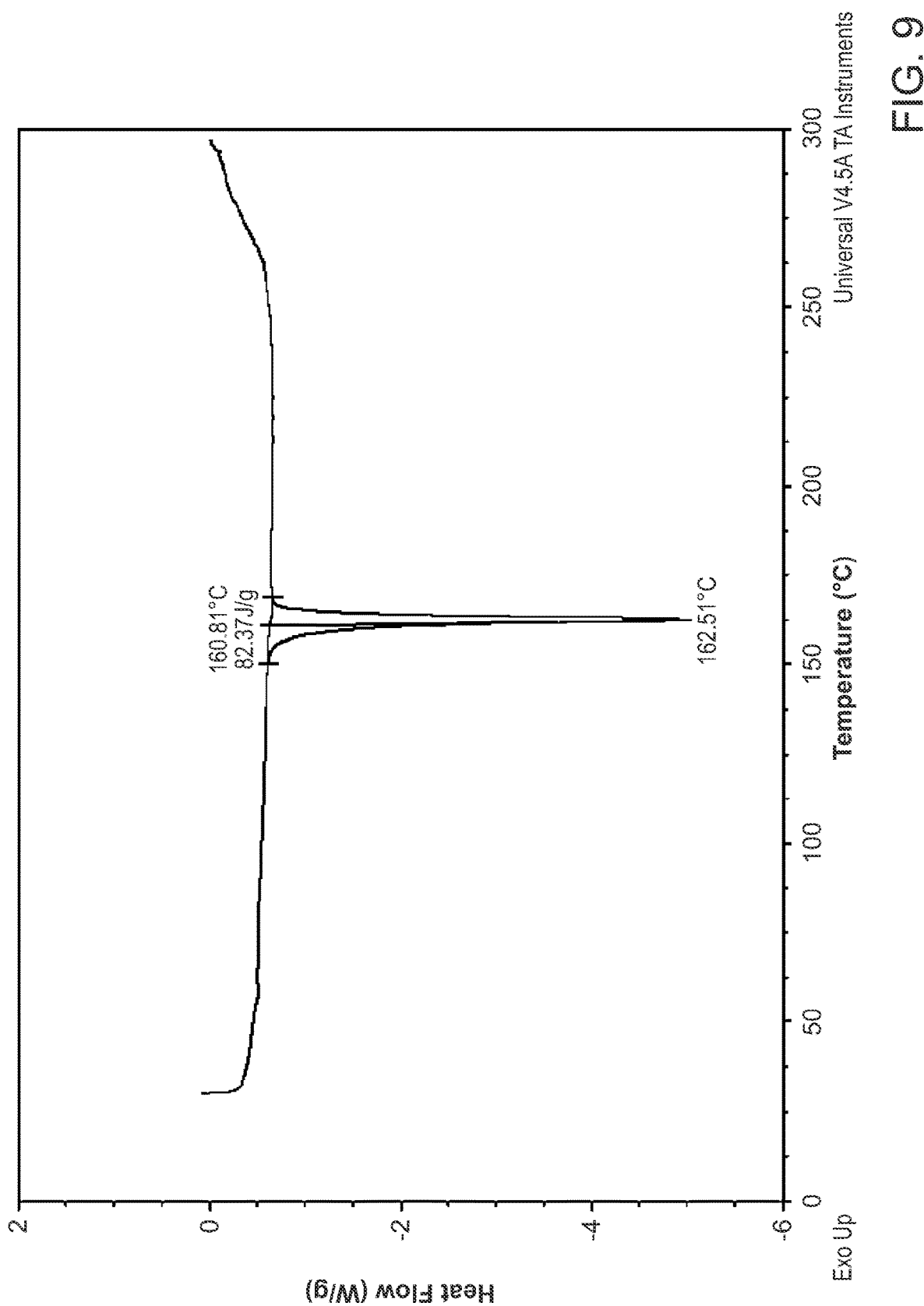
FIG. 9 depicts an exemplary DSC curve of Form 4.

Amorphous Edonentan (100 mg) was added to 2 mL of water containing 0.2 mL of tetrahydrofuran (THF). The resulting mixture was stirred at 50° C. for 24 hours, cooled and filtered to provide Form 4, which was confirmed by XRPD (FIG. 5) and DSC (FIG. 9) to be distinct from Forms 1, 2 and 3.

In an alternate method, 107 mg of amorphous Edonentan was added to 1 mL of water followed by the addition of an equivalent of KOH in 1 mL of water. The resulting solution was heated to 60° C. for 20 minutes, filtered warm and acidified with 1 mL of 0.2 N HCl. The resulting mixture was stirred for 5 hours at 60° C., cooled and filtered to give Form 4, which was confirmed by XRPD.

In an alternate method, 150 mg of Edonentan (Form 3) was added to a mixture of isopropanol and water (1 mL and 2 mL, respectively). The resulting slurry was stirred at 15° C. for 48 hours and then filtered. The sample was confirmed by an XRPD analysis to be Form 4, demonstrating that under these conditions, Form 4 is more thermodynamically stable than Form 3.

In an alternate method, 200 mg of Edonentan (Form 1) was added to a mixture of isopropanol and water (1.3 mL and 2.6 mL, respectively). The resulting solution was heated to 80° C. and stirred for 24 h, then cooled and filtered. The sample thus obtained was confirmed by an XRPD analysis to be Form 4, demonstrating that under these conditions, Form 4 is more thermodynamically stable than Form 1.

In an alternate method, 100 mg of Edonentan (amorphous) was scurried in 10 mL of water and heated to 100° C. for 40 hours. The resulting solution was cooled to ambient temperature and filtered to afford Form 4.

In an alternate method, amorphous (crude) Edonentan is dissolved in 8 volumes of isopropanol at 60° C. The resulting solution is cooled to 57° C., and then a small crystal of the crystalline Form 4 is added. After 2 hours, the solution is cooled to 5° C., held for 15 hours, and filtered to afford the crystalline Form 4.

Example 5: XRPD Pattern of Crystalline Forms

The XRPD patterns of crystalline Forms 1~4 are shown in FIGS. 1-5. The XRPD pattern of the crystalline form described herein was recorded using a Polycrystalline X-ray diffractometer (Bruker, D8 ADVANCE). The CuKa radiation was operating at a voltage of 40 kv and a current of 40 mA with a transmission slit of 1.0 mm and cable-stayed slit of 0.4°. A sample was placed in the center of sample holder groove and the surface of sample holder was leveled with the surface of sample holder. The data were collected over continuous scanning with a step size of 0.02° and a speed of 8°/min using the lynxeye detector.

The following Tables 1~4 list certain XRPD characteristic peaks for crystalline Forms 1-4, respectively.

TABLE 1

Exemplary XRPD patterns of crystalline Form 1

| 2θ | Intensity (counts) |
|---|---|
| 6.3 | 1250 |
| 7.5 | 2750 |
| 11.7 | 1400 |
| 15.1 | 2200 |
| 17.3 | 900 |

TABLE 2

Exemplary XRPD patterns of crystalline Form 2

| Angle [2θ] | Intensity (counts) |
|---|---|
| 9.6 | 2250 |
| 10.4 | 1500 |
| 11.1 | 600 |
| 12.3 | 750 |
| 14.6 | 1000 |
| 15.1 | 800 |
| 17.2 | 1000 |
| 19.6 | 3000 |
| 19.7 | 3000 |
| 22.0 | 1500 |
| 22.9 | 1500 |
| 23.7 | 2000 |

TABLE 3

Exemplary XRPD patterns of crystalline Form 3

| 2θ | Intensity (counts) |
|---|---|
| 7.8 | 2000 |
| 9.0 | 2750 |
| 11.6 | 750 |
| 15.8 | 2500 |
| 19.1 | 900 |

TABLE 4

Exemplary XRPD patterns of crystalline Form 4

| Angle [2θ] | Intensity (counts) |
|---|---|
| 5.6 | 1800 |
| 11.4 | 12600 |
| 14.4 | 1400 |
| 15.7 | 1200 |
| 16.8 | 1400 |
| 17.7 | 4800 |
| 19.3 | 6700 |
| 21.1 | 2900 |
| 21.9 | 2400 |
| 23.9 | 2400 |
| 24.6 | 1900 |

Figure 5:
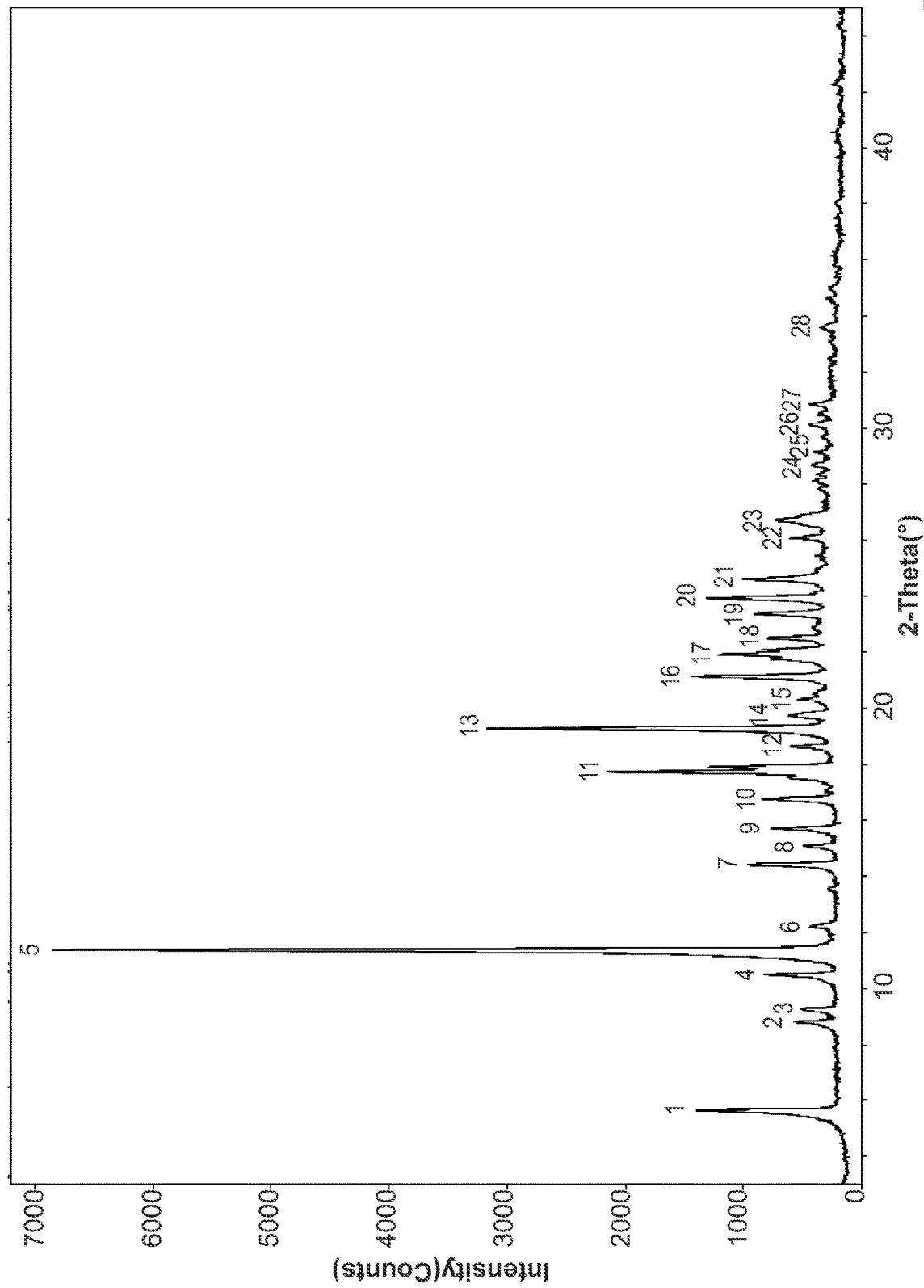
FIG. 5 depicts an exemplary XRPD pattern of Form 4.

Table 5 below lists the XRPD characteristic peaks for crystalline Form 4 shown in FIG. 5.

TABLE 5

XRPD characteristic peaks for crystalline Form 4
SCAN: 3.0/44.9933/0.01973/24 78(sec), Cu(40 kV, 40 mA), I(max) = 6860, Apr. 10, 2020 10:20
PEAK: 35-pts/Parabolic Filter, Threshold = 3.0, Cutoff = 0.1%, BG = 3/1.0, Peak-Top = Summit

| # | 2-Theta | d(A) | Height | I % | Area | I % | FWHM |
|---|---|---|---|---|---|---|---|
| 1 | 5.641 | 15.6528 | 1393 | 20.3 | 13553 | 24.5 | 0.187 |
| 2 | 8.803 | 10.0363 | 563 | 8.2 | 3809 | 6.9 | 0.180 |
| 3 | 9.256 | 9.5470 | 504 | 7.3 | 2976 | 5.4 | 0.169 |
| 4 | 10.494 | 8.4231 | 818 | 11.9 | 4742 | 8.6 | 0.134 |
| 5 | 11.367 | 7.7780 | 6860 | 100.0 | 55374 | 100.0 | 0.140 |
| 6 | 12.198 | 7.2497 | 434 | 6.3 | 1350 | 2.4 | 0.117 |
| 7 | 14.408 | 6.1424 | 951 | 13.9 | 6234 | 11.3 | 0.141 |
| 8 | 15.072 | 5.8734 | 484 | 7.1 | 1747 | 3.2 | 0.110 |
| 9 | 15.710 | 5.6362 | 764 | 11.1 | 4042 | 7.3 | 0.124 |
| 10 | 16.773 | 5.2814 | 839 | 12.2 | 3958 | 7.1 | 0.113 |
| 11 | 17.739 | 4.9959 | 2150 | 31.3 | 20631 | 37.3 | 0.183 |
| 12 | 18.629 | 4.7591 | 595 | 8.7 | 1999 | 3.6 | 0.109 |
| 13 | 19.280 | 4.5999 | 3173 | 46.3 | 23625 | 42.7 | 0.137 |
| 14 | 19.733 | 4.4952 | 608 | 8.9 | 3384 | 6.1 | 0.180 |
| 15 | 20.295 | 4.3721 | 536 | 7.8 | 2106 | 3.8 | 0.151 |
| 16 | 21.132 | 4.2006 | 1439 | 21.0 | 8311 | 15.0 | 0.124 |
| 17 | 21.907 | 4.0538 | 1206 | 17.6 | 11523 | 20.8 | 0.222 |
| 18 | 22.495 | 3.9493 | 795 | 11.6 | 3003 | 5.4 | 0.112 |
| 19 | 23.365 | 3.8041 | 903 | 13.2 | 4778 | 8.6 | 0.141 |

TABLE 5-continued

XRPD characteristic peaks for crystalline Form 4
SCAN: 3.0/44.9933/0.01973/24 78(sec), Cu(40 kV,
40 mA), I(max) = 6860, Apr. 10, 2020 10:20
PEAK: 35-pts/Parabolic Filter, Threshold = 3.0,
Cutoff = 0.1%, BG = 3/1.0, Peak-Top = Summit

| # | 2-Theta | d(A) | Height | I % | Area | I % | FWHM |
|---|---------|------|--------|-----|------|-----|------|
| 20 | 23.938 | 3.7143 | 1304 | 19.0 | 7676 | 13.9 | 0.133 |
| 21 | 24.624 | 3.6123 | 995 | 14.5 | 7730 | 14.0 | 0.189 |
| 22 | 26.073 | 3.4148 | 595 | 8.7 | 2572 | 4.6 | 0.146 |
| 23 | 26.718 | 3.3338 | 722 | 10.5 | 7595 | 13.7 | 0.294 |
| 24 | 28.674 | 3.1107 | 412 | 6.0 | 1069 | 1.9 | 0.142 |
| 25 | 29.141 | 3.0619 | 398 | 5.8 | 754 | 1.4 | 0.098 |
| 26 | 30.115 | 2.9650 | 440 | 6.4 | 3479 | 6.3 | 0.309 |
| 27 | 30.841 | 2.8969 | 437 | 6.4 | 1605 | 2.9 | 0.152 |
| 28 | 33.588 | 2.6660 | 345 | 5.0 | 2082 | 3.8 | 0.259 |

NOTE:
Intensity = Counts, 2T(0) = 0.0(°), Wavelength to Compute d-Spacing = 1.54056A(Cu/K-alpha1)

Example 6: Physiochemical Properties of Crystalline Forms

Provided herein are exemplary physicochemical properties of crystalline forms. The melting points described herein can be measured using the following procedure:

Melting Point Protocol

The maximal melting point peak ($T_m$) of each crystalline form was determined using DSC. The DSC of the crystalline form described herein was measured using the TA instrument DSC Q2000. A sample (1.3010 mg) was weighed in an aluminum crucible and heated from 30° C. to 300° C. at a heating rate of 10° C./min. Temperatures at crystalline melting peak start, peak onset, peak max, and peak end were collected.

The solubility described herein can be measured using the following procedure:

Solubility Analysis Protocol

1. No less than 2.0 mg samples are weighed into lower chamber of whatman miniuniprep vials (GE Healthcare). 450 µL of buffer was added into each chamber.

2. Filter pistons of miniuniprep vials are placed and compressed to the position of the liquid level to allow for contact of buffer and compound with the filter during incubation.

3. The samples are vortexed for 2 minutes followed by incubation at room temperature (about 25±2° C.) for 24 hours with shaking at 500 rpm.

4. Miniunipreps are compressed to prepare the filtrates for injection into HPLC system. All vials are inspected for visible undissolved material before filtering and for leakage after filtering.

5. Dilute supernatant with buffer by a factor of 100 folds to make diluents which are analyzed with HPLC.

Provided in Table 6 below are exemplary physicochemical properties of crystalline Forms 1-4. The physicochemical properties can be obtained using the methods described above.

TABLE 6

Exemplary physicochemical properties of crystalline Forms 1-4

| Polymorph | Solvation | $T_m$ (° C.) | Solubility pH 7.0 Phosphate Buffer (µg/mL) |
|-----------|-----------|--------------|--------------------------------------------|
| Form 1 | anhydrate | 151 | 264 |
| Form 2 | monohydrate | 122 | 35 |
| Form 3 | anhydrate | 162 | 251 |
| Form 4 | anhydrate | 163 | 138 |

Among the four crystalline forms, Form 4 exhibited higher melting point ($T_m$) than Form 1 and Form 2. Form 4 exhibited lower solubility than Form 1 and Form 3. Form 4 demonstrated higher thermodynamic stability compared to Form 1, Form 2 and Form 3, as depicted above. In preferred embodiments, Form 4 is preferable for pharmaceutical development.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

Further, from the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A solid form of a compound of Formula I:

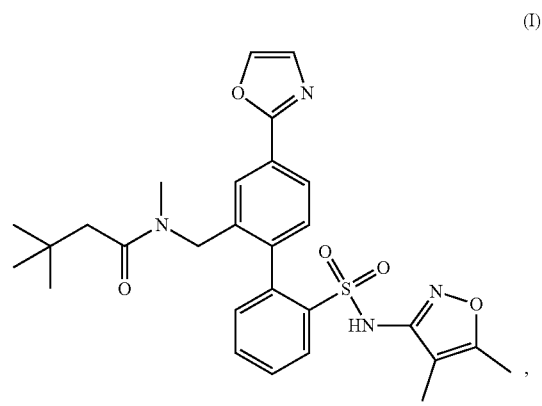 [SMILES: Cc1onc(NS(=O)(=O)c2ccccc2-c2ccc(-c3ncco3)cc2CN(C)C(=O)CC(C)(C)C)c1C]

(I)

wherein
said compound is an anhydrous crystalline form, having an X-ray powder diffraction pattern comprising at least three characterization peaks, in terms of diffraction angle (2θ), wherein the peaks are selected from 5.6±0.2°, 11.4±0.2°, 17.7±0.2°, 19.3±0.2°, 21.1±0.2°, and 21.9±0.2°.

2. The solid form of claim 1, wherein the anhydrous crystalline form comprises the following characteristic peaks expressed in terms of diffraction angles (2θ): 11.4±0.2°, 17.7±0.2°, and 19.3±0.2°.

3. The solid form of claim 1, wherein the anhydrous crystalline form comprises the following characteristic peaks expressed in terms of diffraction angles (2θ): 11.4±0.2°, 17.7±0.2°, 19.3±0.2°, and 21.1±0.2°.

4. The solid form of claim 1, wherein the anhydrous crystalline form comprises the following characteristic peaks expressed in terms of diffraction angles (2θ): 5.6±0.2°, 11.4±0.2°, 17.7±0.2°, 19.3±0.2°, 21.1±0.2°, and 21.9±0.2°.

5. The solid form of claim 1, wherein the anhydrous crystalline form comprises the following characteristic peaks expressed in terms of diffraction angles (2θ): 5.6±0.2°, 11.4±0.2°, 14.4±0.2°, 15.7±0.2°, 16.8±0.2°, 17.7±0.2°, 19.3±0.2°, 21.1±0.2°, 21.9±0.2°, 23.9±0.2° and 24.6±0.2°.

6. The solid form of claim 1, wherein the anhydrous crystalline form has a $T_m$ of about 163° C. by differential scanning calorimetry (DSC) analysis.

7. The solid form of claim 1, wherein the anhydrous crystalline form has a solubility of about 138 μg/mL at pH 7.0 in phosphate buffer.

8. A method of preparing an anhydrous crystalline form of a compound of Formula I:

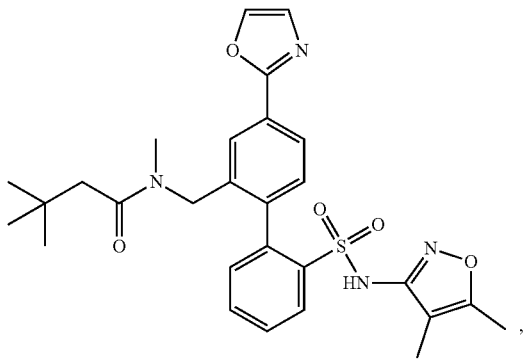

(I)

the method comprising:
(a) stirring the compound of Formula I in an aqueous solution, an organic solvent, or a mixture thereof, at a temperature in the range of about 40° C. to about 120° C.;
(b) cooling the resulting solution to a temperature in the range of about 0° C. to about room temperature; and
(c) filtering the sample to afford the anhydrous crystalline form,
wherein said anhydrous crystalline form has an X-ray powder diffraction pattern comprising at least three characterization peaks, in terms of 2θ, wherein the peaks are selected from 5.6±0.2°, 11.4±0.2°, 17.7±0.2°, 19.3±0.2°, 21.1±0.2°, and 21.9±0.2°.

9. The method of claim 8, wherein the method further comprises seeding an amount of an anhydrous crystalline form, wherein the anhydrous crystalline form comprises the following characteristic peaks expressed in terms of diffraction angles (2θ): 5.6±0.2°, 11.4±0.2°, 14.4±0.2°, 15.7±0.2°, 16.8±0.2°, 17.7±0.2°, 19.3±0.2°, 21.1±0.2°, 21.9±0.2°, 23.9±0.2° and 24.6±0.2°.

10. The method of claim 8, wherein the temperature for stirring is in the range of about 40° C. to about 80° C.

11. The method of claim 8, wherein the temperature for stirring is about 70° C.

12. The method of claim 8, wherein the stirring takes place for about 20 hours.

13. The method of claim 8, wherein a slurry of the compound of Formula I is formed in the stirring step.

14. The method of claim 8, wherein the aqueous solution is water.

15. The method of claim 8, wherein the organic solvent is a water-soluble organic solvent.

16. The method of claim 8, wherein the organic solvent is isopropanol.

17. The method of claim 8, wherein the cooling occurs at about 5° C. for about 15 hours.

18. The method of claim 8, wherein the anhydrous crystalline form comprises the following characteristic peaks expressed in terms of diffraction angles (2θ): 11.4±0.2°, 17.7±0.2°, and 19.3±0.2°.

19. The method of claim 8, wherein the anhydrous crystalline form comprises the following characteristic peaks expressed in terms of diffraction angles (2θ): 5.6±0.2°, 11.4±0.2°, 17.7±0.2°, 19.3±0.2°, 21.1±0.2°, and 21.9±0.2°.

20. The method of claim 8, wherein the anhydrous crystalline form comprises the following characteristic peaks expressed in terms of diffraction angles (2θ): 5.6±0.2°, 11.4±0.2°, 14.4±0.2°, 15.7±0.2°, 16.8±0.2°, 17.7±0.2°, 19.3±0.2°, 21.1±0.2°, 21.9±0.2°, 23.9±0.2° and 24.6±0.2°.

* * * * *